Figure 1:
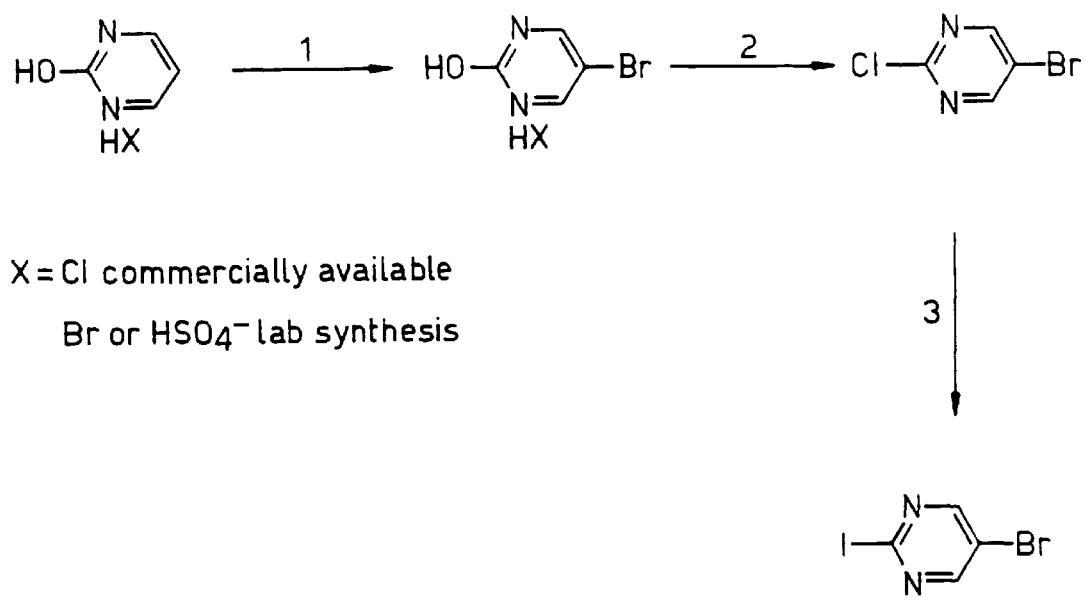

United States Patent [19]
Lewis et al.

[11] Patent Number: 5,986,096
[45] Date of Patent: Nov. 16, 1999

[54] PYRIMIDINE COMPOUNDS

[75] Inventors: Robert Andrews Lewis; John William Goodby; Kenneth Johnson Toyne; Michael Hird, all of Hull, United Kingdom

[73] Assignee: The Secretary of State for Defence in Her Britannic Majesty's a Government of the U.K. of Gt. Britain & N. Ireland of Defence Evaluation & Research Agency, United Kingdom

[21] Appl. No.: 08/913,968

[22] PCT Filed: Mar. 23, 1996

[86] PCT No.: PCT/GB96/00866

§ 371 Date: Sep. 25, 1997

§ 102(e) Date: Sep. 25, 1997

[87] PCT Pub. No.: WO96/30344

PCT Pub. Date: Oct. 3, 1996

[30] Foreign Application Priority Data

Mar. 28, 1995 [GB] United Kingdom .................. 9506309

[51] Int. Cl.[6] .......................... C07D 239/40; C09K 19/32
[52] U.S. Cl. ...................... 544/334; 544/335; 252/299.62
[58] Field of Search ....................................... 544/334, 335

[56] References Cited

FOREIGN PATENT DOCUMENTS

| | | |
|---|---|---|
| 0 225 195 | 6/1987 | European Pat. Off. . |
| 0 255 962 | 2/1988 | European Pat. Off. . |
| 0 278 665 | 8/1988 | European Pat. Off. . |
| 0 332 025 | 9/1989 | European Pat. Off. . |
| 0 438 811 A2 | 7/1991 | European Pat. Off. . |
| 0 611 119 A2 | 8/1994 | European Pat. Off. . |
| 332024 | 9/1998 | European Pat. Off. . |
| WO 88/07523 | 10/1988 | WIPO . |
| WO 90/13611 | 11/1990 | WIPO . |
| WO 90/15116 | 12/1990 | WIPO . |
| WO 96/01246 | 1/1996 | WIPO . |
| WO 96/30344 | 10/1996 | WIPO . |

OTHER PUBLICATIONS

The Merk Index, tenth edition, p. 692, entry 4678, 1983.

Liquid Crystals, 1993, vol. 14, No. 3, 741–761 Hird et al Palladium–catalysed cross–coupling reactions in the synthesis of some high polarizability materials.

Mol. Cryst. Liq. Cryst. 1991, vol. 206, pp. 187–204 Hird et al Cross–Coupling Reactions in the Synthesis of Liquid Crystals.

Mol. Cryst. Liq. Cryst. 1991, vol. 104, pp. 91–110 Gray et al Some Developments in the Synthesis of Liquid Crystals.

*Primary Examiner*—John M. Ford
*Assistant Examiner*—Pavanaram K Sripada
*Attorney, Agent, or Firm*—Nixon & Vanderhye

[57] ABSTRACT

5-Bromo-2-iodopyrimidine is used to synthesize a range of chemical compounds including liquid crystalline compounds.

15 Claims, 9 Drawing Sheets

X = Cl commercially available
Br or HSO4⁻ lab synthesis

PYRIMIDINE COMPOUNDS

This application is a 371 of PCT/9B96/00866 filed on Mar. 23, 1996.

This invention relates to pyrimidine containing compounds.

Pyrimidine is generally referred to as a heterocycle and has the following structure:

Pyrimidine occurs in a large number of natural products.

Pyrimidine containing compounds and derivatives of pyrimidine containing compounds are used in a broad range of applications throughout the chemical and other industries. There are various synthetic methods which are used in order to incorporate pyrimidine into target molecules.

The synthesis of many chemical compounds is a long and arduous business. Research chemists are continually looking for ways in which to improve the ease of synthesis and subsequent yields and to synthesise new compounds.

One area in particular in which the incorporation of a pyrimidine ring into a target molecule has received much attention is in liquid crystal chemistry.

There are a number of known liquid crystal systems which contain one or more pyrimidine rings.

Some of the many examples include the phenyl-pyrimidines described in WO 86/00083, which describes a series of optically active liquid crystal compounds that contain the chiral group:

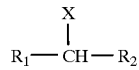

where X represents Cl, CN or $CH_3$ and $R_1$ and $R_2$ represent the residue of the molecule. All of the compounds described necessarily contain the phenyl-pyrimidine group on the mesogenic unit.

The difluoro-phenyl pyrimidines described in European Patent Application EP 0 332 024 A1:

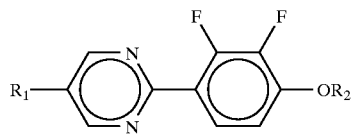

including those compounds where $R_1$ and $R_2$ are independently $C_3$–$C_9$ alkyl. There are numerous other pyrimidine compounds described in EP 0 332 024 A1.

It is known to incorporate pyrimidine into liquid crystal molecules. For example in Molecular Crystals and Liquid Crystals, 1971, vol. 15 pp161–74, and references therein, Demus et al describe a cyclization process for the incorporation of a pyrimidine into a target molecule. Similarly Zaschke in Journal f. prakt. Chemie, vol 317, part 4, 1975, S, 617–630 describe the synthesis of pyrimidine containing compounds via cyclization reactions. Typically an amidine

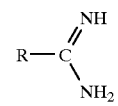

is reacted with a diester or diacetal. This method is still used for synthesising pyrimidine containing compounds, for example see the article by Kelly and Fünfschilling in J. Mater. Chem., 1993, 3(9), 953-63.

The following compounds are well known to those skilled in the field as liquid crystal compounds:

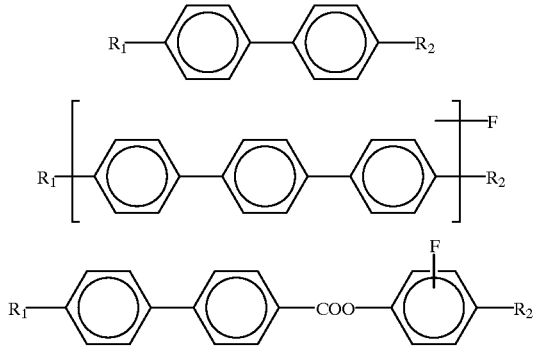

for the above compounds the following terminology is generally used:

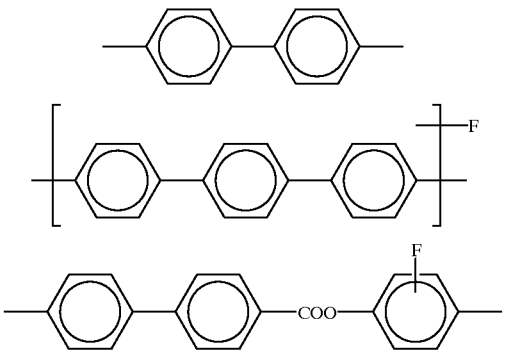

are referred to as molecular cores wherein COO is a linking group and $R_1$ and $R_2$ are generally referred to as terminal groups. Generally a pyrimidine ring would be incorporated into the core of the molecule.

In order to incorporate a pyrimidine in to the core of a molecule then a so-called coupling reaction may be carried out. Generally the connection of two alkyl or two aryl groups is called a coupling reaction. There are both symmetrical and unsymmetrical coupling reactions. Unsymmetrical coupling reactions are also called cross-coupling reactions.

In Liquid Crystals 1993, 14, 741–61 comments on the use of

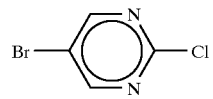

are provided as well as details of its synthesis. This compound is also discussed in Mol. Cryst. Liq. Cryst., 1991, 206, 187–204 and Mol. Cryst. Liq. Cryst., 1991, 204, 91–110.

There are limitations associated with the use of

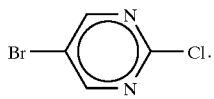

The groups Br and Cl may be referred to as leaving groups. It is important in many chemical reactions that potential leaving groups are of different reactivity. One of the problems associated with the compound above is that the Br is more likely to act as a leaving group than is the Cl. This means that it is impossible to attach a group to the chlorine end of the pyrimidine ring first thus limiting the use of such a compound for the incorporation of a pyrimidine ring into target molecules.

It is also difficult to prepare the following compound in a pure form:

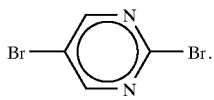

Typically this is prepared as follows:

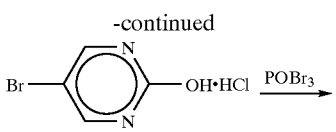

-continued

 POBr₃ →

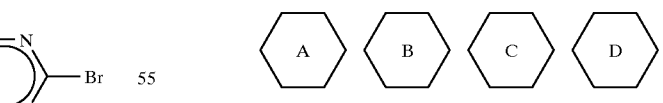

The final compound tends to be a mixture of bromo and chloro containing compounds.

The current invention seeks to alleviate the above problems relating to the synthesis of pyrimidine containing compounds by the provision of a novel pyrimidine containing compound.

According to this invention a compound of the following formula I is provided:

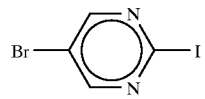

According to a further aspect of this invention a method for the production of formula I is provided comprising the steps:

mixing a compound of formula II

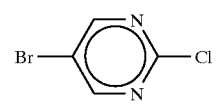

with a source of iodine.

Preferably the source of iodine is hydrogen iodide and even more preferably the hydrogen iodide is in aqueous solution.

The reaction may be carried out in aqueous solution and there may be a co-solvent present.

According to a further aspect of the invention materials of formula III are provided:

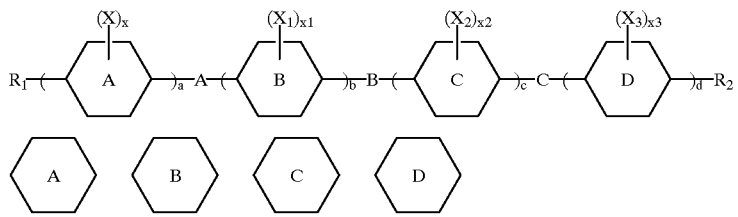

are independently chosen from phenyl, cyclohexyl, pyrimidine, pyridine, dioxanyl, thiophene: provided at least one of is chosen from pyrimidine;

$X, X_1, X_2, X_3$ are independently chosen from F, Cl, CN;

$x, x1, x2, x3$ are independently chosen from 0, 1. 2, 3;

$R_1$ is chosen from $C_{1-16}$ alkyl or alkoxy or $CF_3$ or F or CN;

$R_2$ is chosen from $C_{1-16}$ alkyl or alkoxy or $C{\equiv}C\text{-}R_3$ wherein $R_3$ is $C_{1-12}$ alkyl;

R₂ may also be chosen from the following:

$$O(CH_2)_{1-4}-\underset{R_2}{\overset{Y}{\underset{|}{\overset{|}{C}}}}-R_1$$

wherein Y is chosen from F, Cl, CN, H, R₁ and R₂ are independently selected from C$_{1-12}$ branched or straight chain alkyl or H provided that R₁ and R₂ and Y are different;

$$CO_2-(CH_2)_{0-6}-\underset{R_2}{\overset{Y}{\underset{|}{\overset{|}{C}}}}-R_1$$

wherein Y is chosen from F, Cl, CN, H, R₁ and R₂ are independently selected from C$_{1-12}$ branched or straight chain alkyl or H provided that R₁ and R₂ and Y are different;

OCO-CH(Z)-CH(Z₁)-(CH₂)$_{1-6}$CH₃ wherein Z is chosen from F, Cl, CN and Z₁ is chosen from C$_{1-6}$ alkyl;

A, B, C are chosen independently from single bond, alkyne, CO₂, OCO;

a, b, c, d may be 0 or 1 provided that a+b+c+d>1.

The compound of formula I may also be used for the synthesis of known compounds which may or may not be liquid crystalline wherein these compounds contain one or more pyrimidine rings.

5-bromo-2-iodopyrimidine may be used in the synthesis of compounds which contain the following units:

[structure: phenyl-pyrimidine-(O)R or (S)R or (O)COR or CO₂R, with F substituent]

none of which are easily obtainable from the following:

[structure: Br-pyrimidine-Cl]

Some examples of known compounds are illustrated below.

[structure: RO-pyrimidine-phenyl-CN]

[structure: RO-pyrimidine-phenyl-R', OR']

[structure: RO-pyrimidine-difluorophenyl-OR]

[structure: RO-phenyl(F)(F)-pyrimidine-phenyl(F)(F)-CN, OR', R']

[structure: RO-pyrimidine-phenyl(F)(F)(F)(F)-F, CF₃, OCF₃, OCHF₂, OCH₂CF₃]

[structure: RO-pyrimidine-phenyl(F)(F)-CO₂-phenyl(F)(F)-OR', R']

wherein R and R' are alkyl groups.

Coupling reactions may be used to create aryl and alkynyl linked pyrimidine systems.

It is possible to link a number of units capable of creating C-C bonds. For example:

Ar—B(OH)₂,

Ar—Zn—Cl,

—C≡C—Zn—Cl, $$\text{\textbackslash}C=C\text{\textbackslash}_{ZnCl}$$

[structure: X-O-B-R-O cyclic boronate]

[structure: Ar—B(O-(CH₂)₃-O) wherein X may (CH₂)₂ or 3]

For further details see Mol. Cryst. Liq. Cryst., 1991, vol 206, pp187–204. There are many suitable catalysts for coupling reactions including Pd(PPh₃)₄ which may be introduced in the form of Pd(PPh₃)₂Cl₂.

It may be possible to displace the 2-iodo substituent by nucleophilic attack for example to make carbon—carbon bonds.

There are numerous advantages associated in using 5-bromo-2-iodopyrimidine to prepare pyrimidine containing compounds, including the following:

Speed and ease of synthesis,

High yields. In particular high yields may be obtained by the convergent palladium catalysed cross-coupling methodology, The cyclization method detailed in references mentioned above requires a new synthetic process for each homologue prepared, whereas the method detailed here based on palladium catalysed cross-coupling methodology is a convergent synthesis, therefore stocks of certain units may be used in the synthesis of other homologues, There are many types of pyrimidine containing compounds for which it is extremely difficult to synthesise target molecules using known methods; examples of such compounds include those containing a terminal alkoxy chain on the pyrimidine. It is also difficult to synthesise substituted, for example, fluoro and difluoro-phenylpyrimidines using existing techniques due to the directing effects of the fluoro-substituents giving rise to an undesired substitution pattern, Less cost. The low yields and extra labour costs of existing methodology makes the costs considerably lower when using palladium catalysed cross-coupling techniques, Increased safety. Fewer reactions are used in the new process which means significantly less contact with chemicals and less waste is produced.

Figure 10:
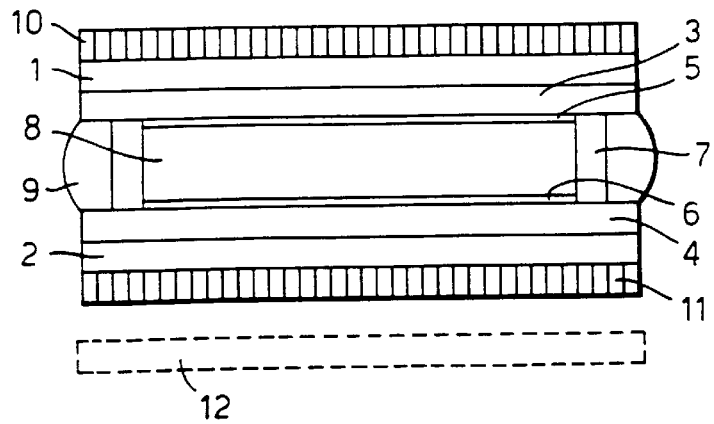

The invention will now be described with reference to the following diagrams:

FIG. 1 illustrates a synthetic route for the synthesis of 5-bromo-2-iodopyrimidine, FIGS. 2–9 illustrates synthetic routes for the synthesis of compounds described by the current invention, FIG. 10 illustrates a liquid crystal device incorporating materials described by the current invention.

The following reagents correspond to the synthetic schemes in FIGS. 1–9:

FIG. 1:
1/ $Br_2/H_2O$
2/ $POCl_3$
3/ $HI/CH_2Cl_2$

Figure 2:
Figure 2:
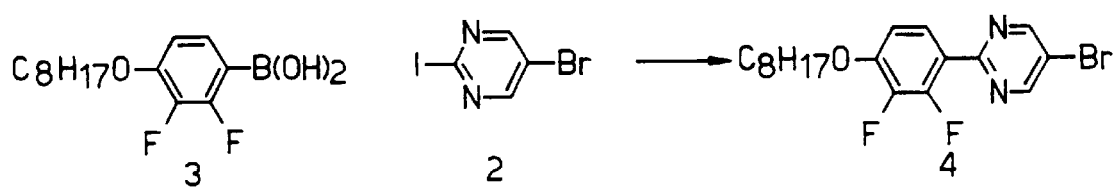
Figure 2:
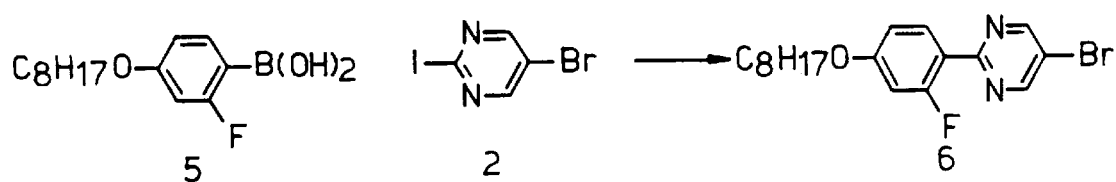
Figure 2:
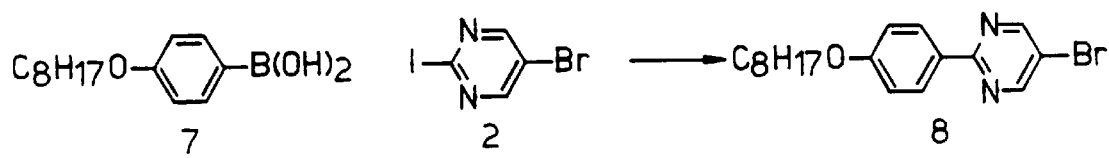
Figure 2:
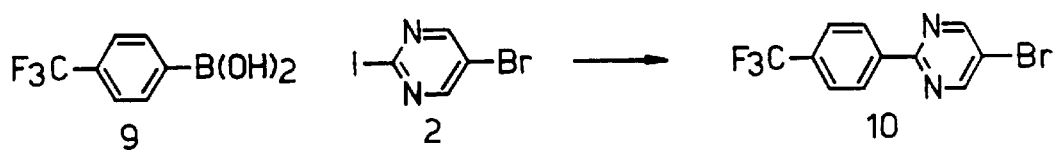
Figure 2:
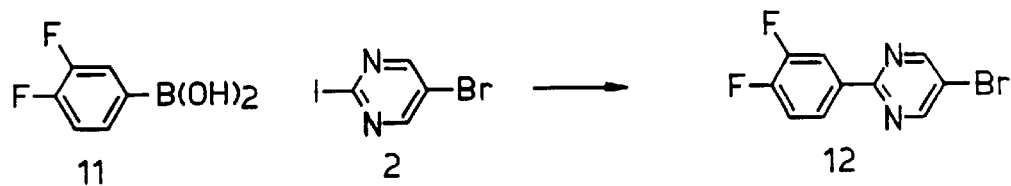
Figure 3:
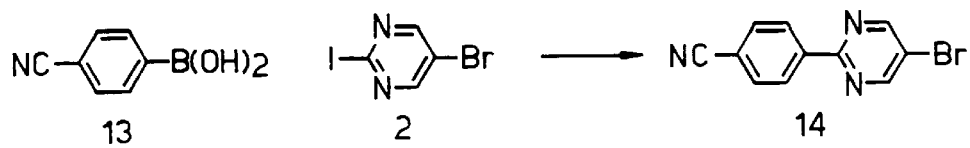
Figure 3:
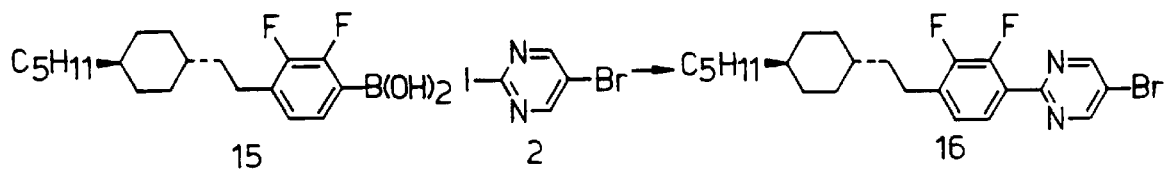
Figure 3:
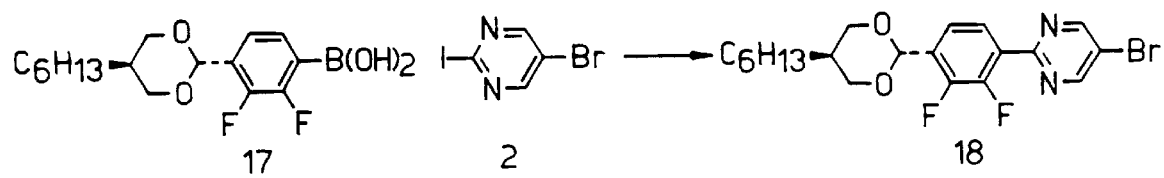
Figure 3:
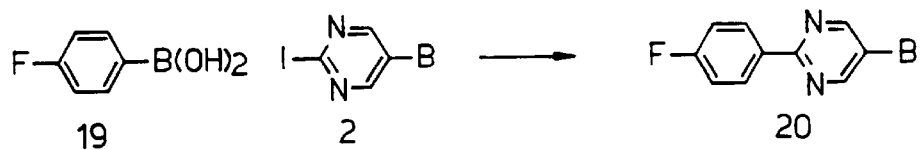
Figure 3:
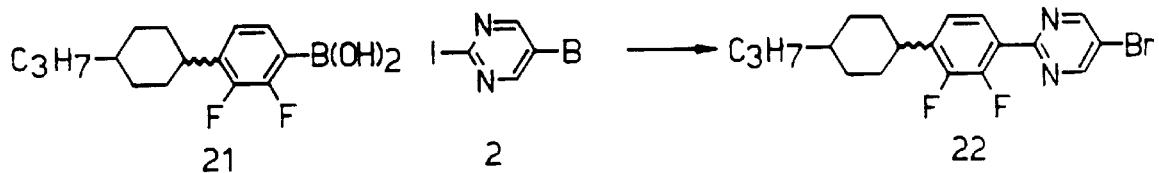
Figure 3:
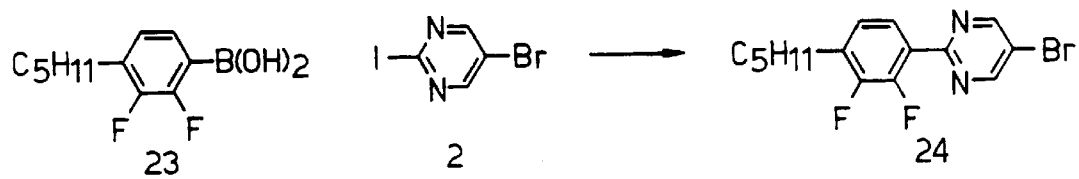
Figure 3:
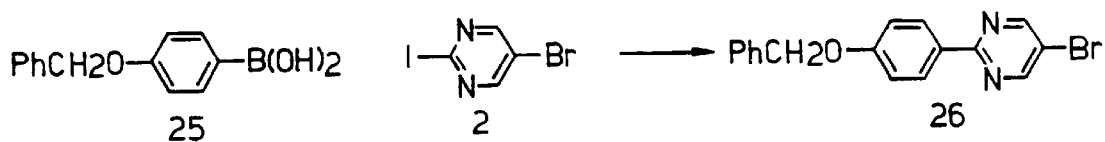
Figure 4:
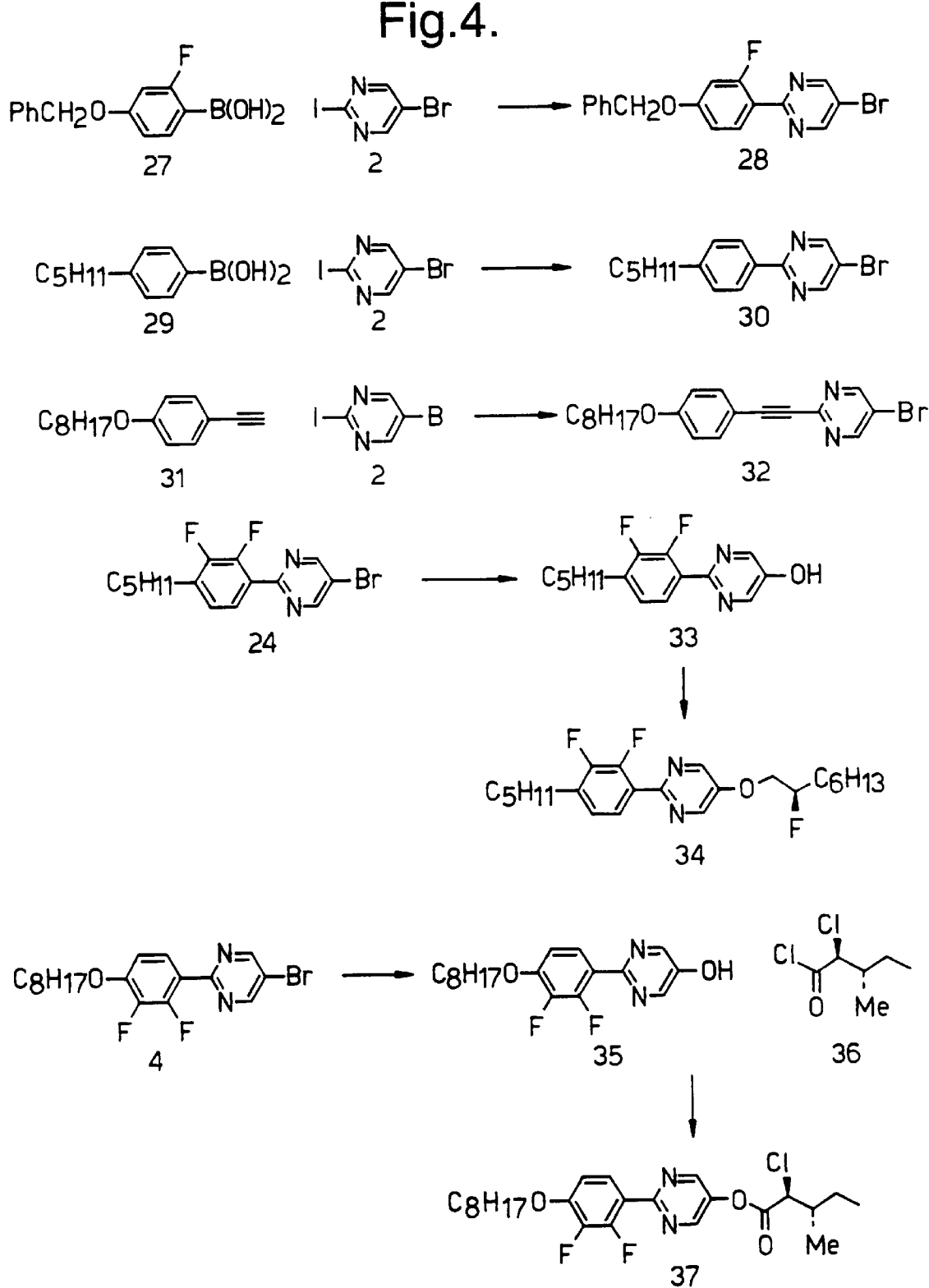
Figure 5:
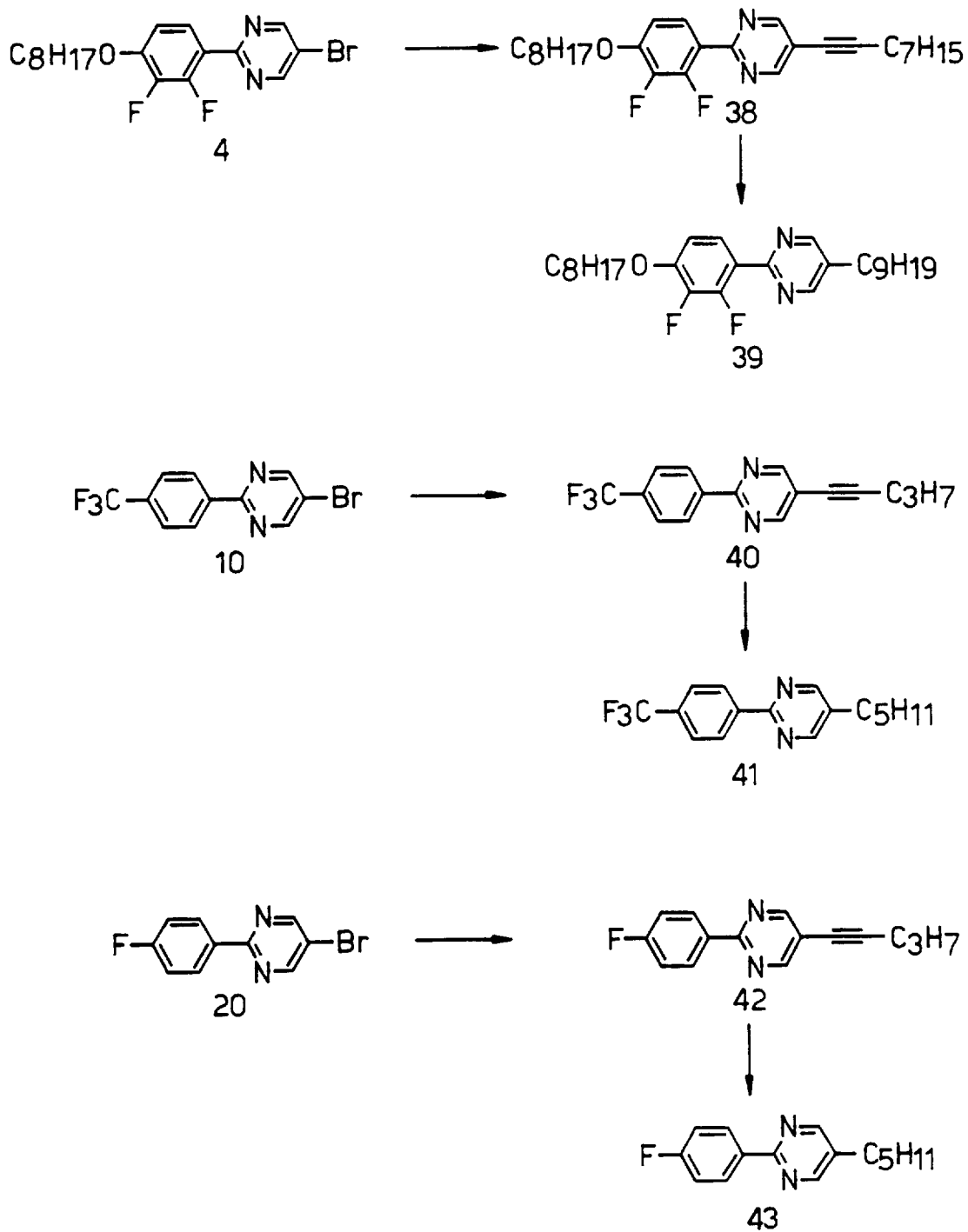
Figure 6:
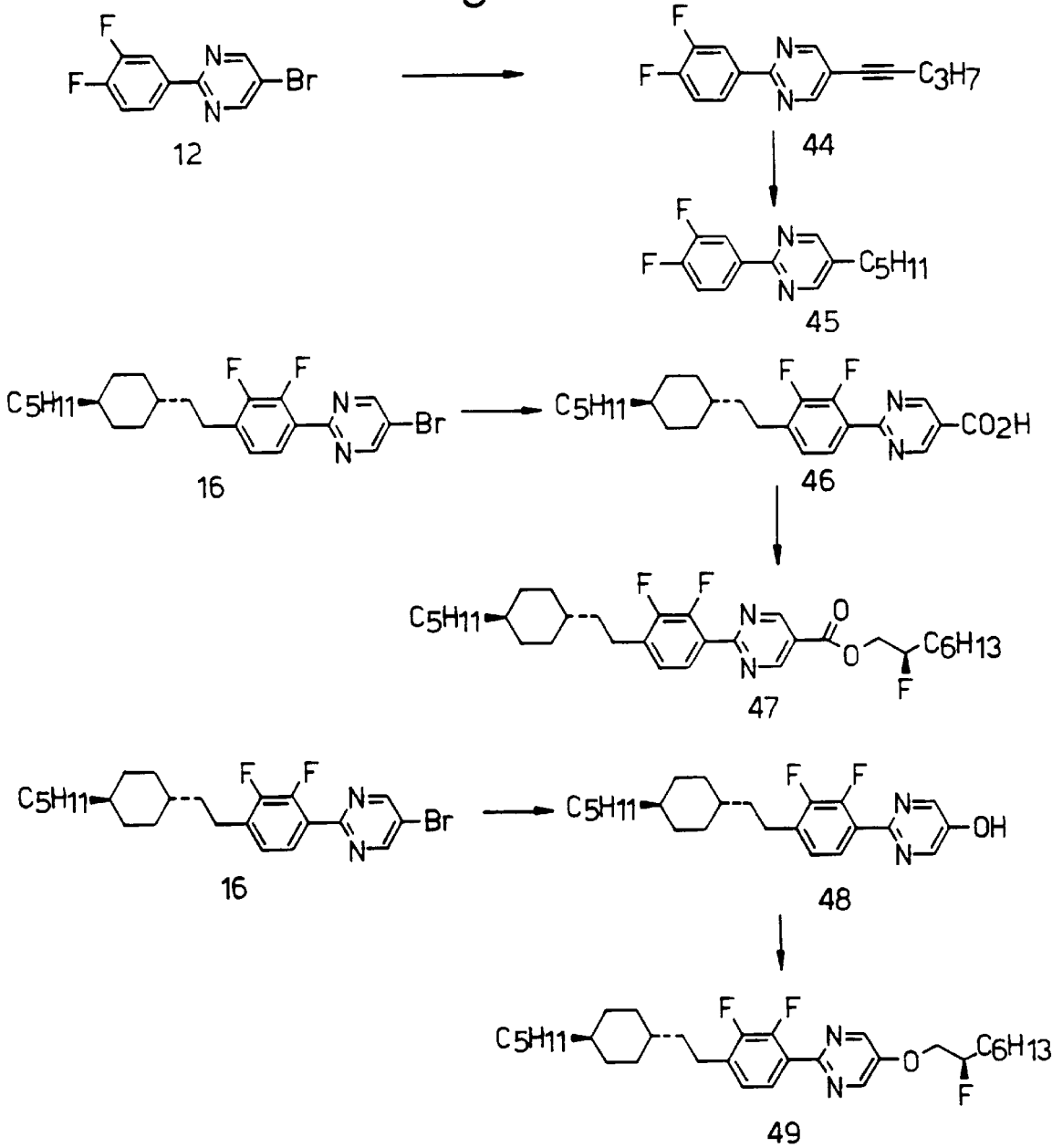
Figure 7:
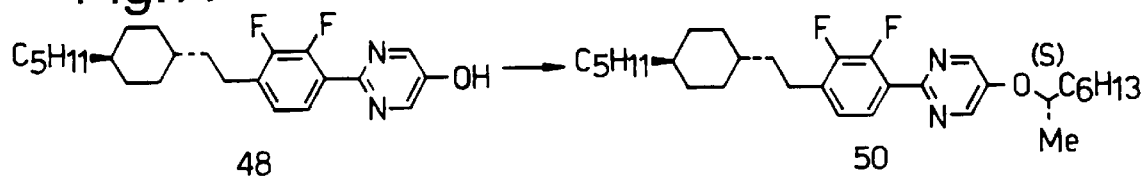
Figure 7:
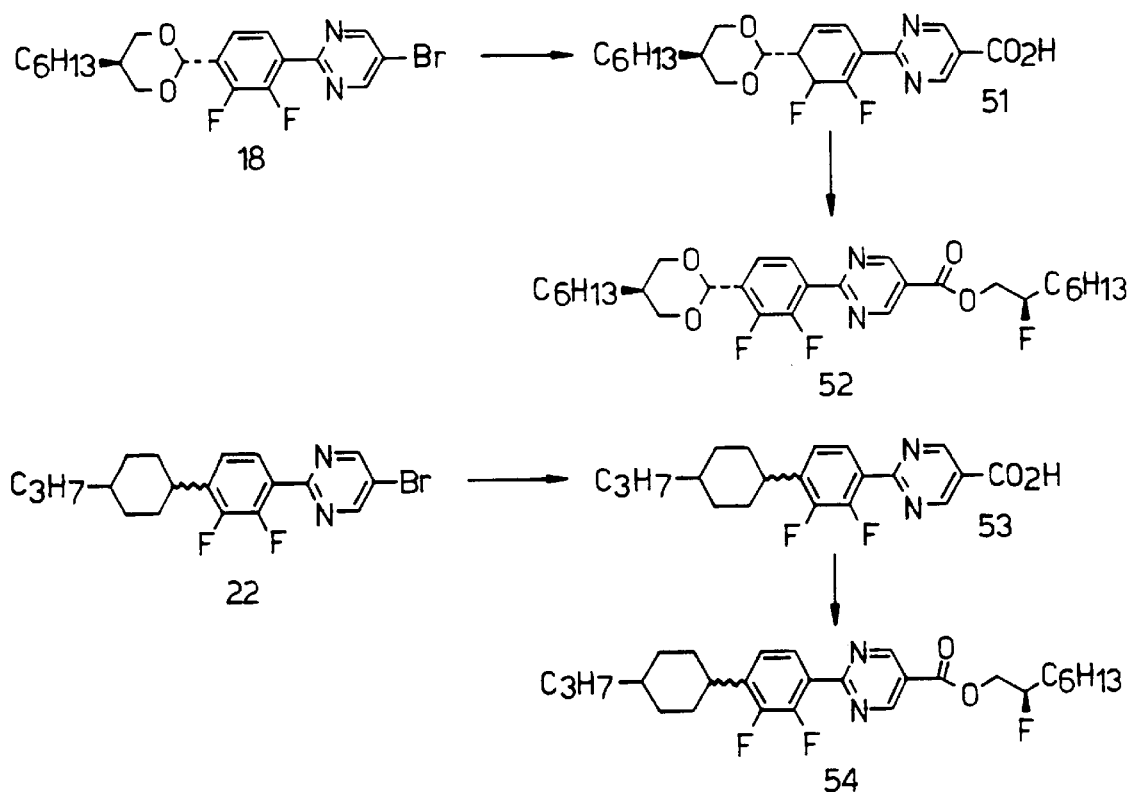
Figure 8:
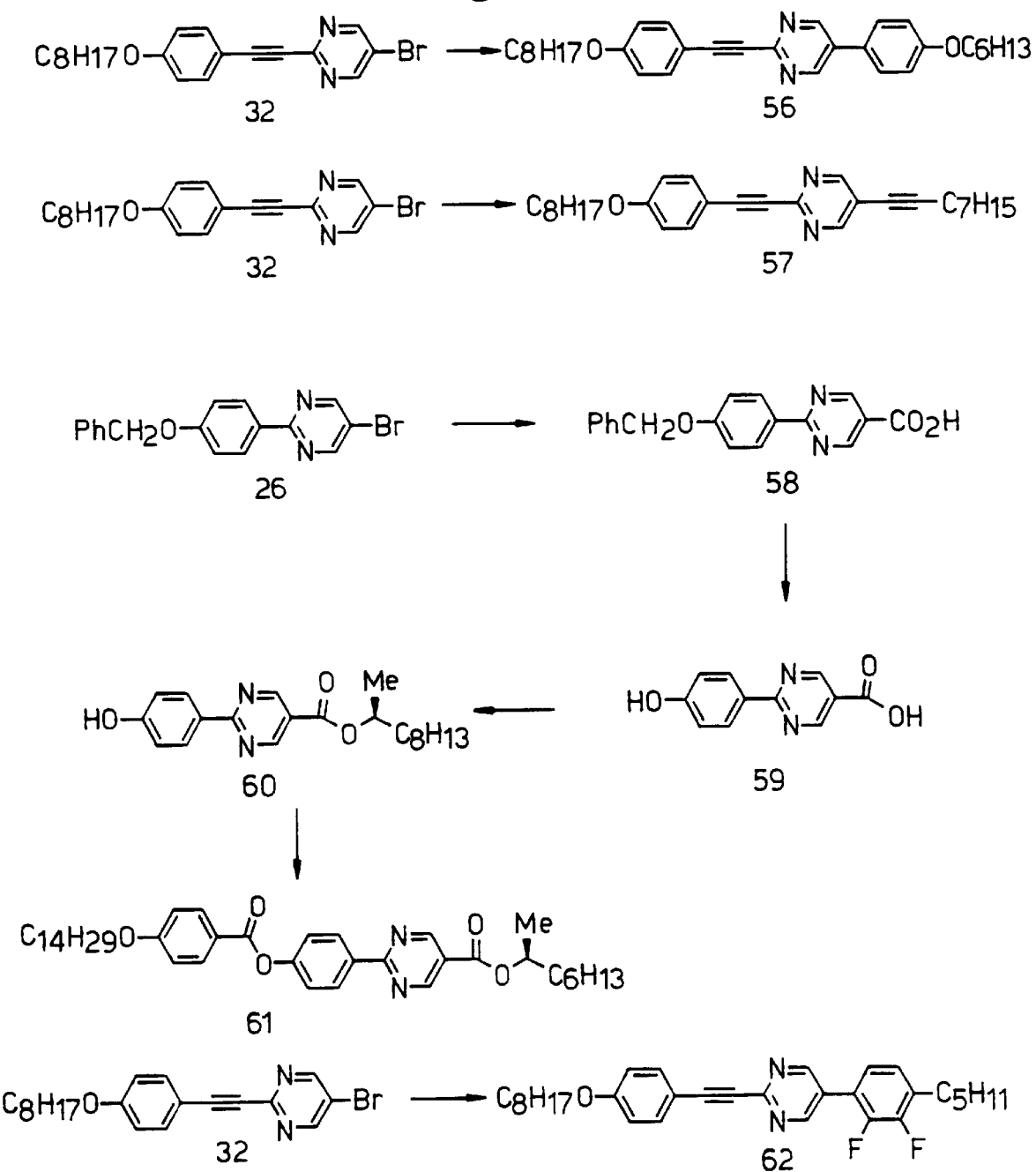
Figure 9:
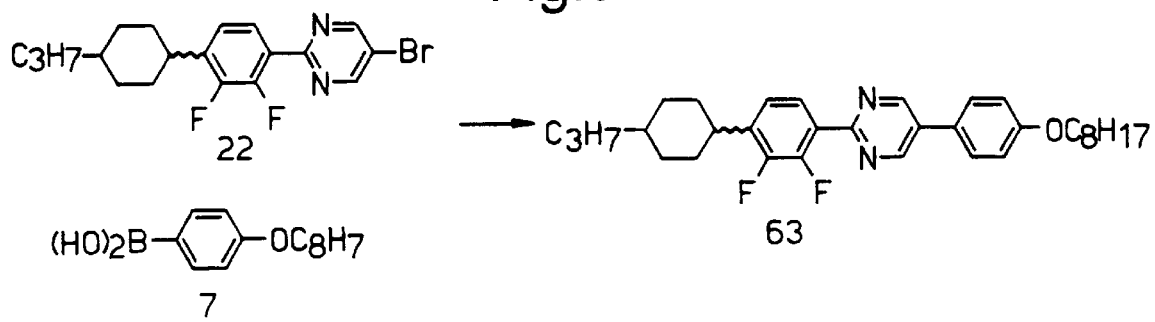
Figure 9:
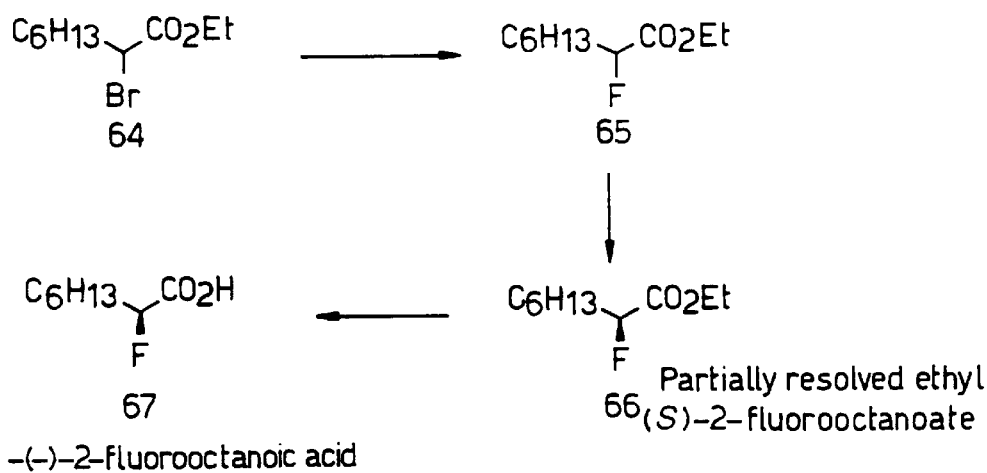
Figure 9:
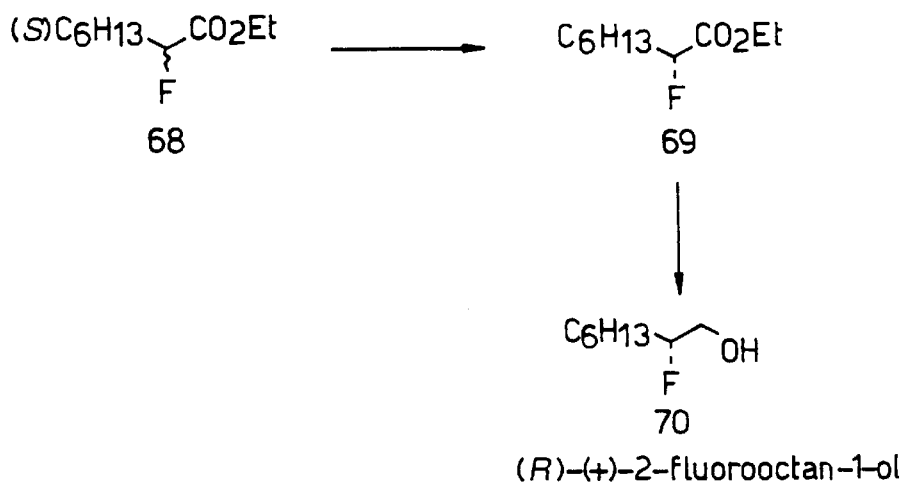

FIG. 2:
1/ 57% hydriodic acid, dichloromethane 0° C.
2/ $Pd(PPh_3)_4$, DME, 2M $Na_2CO_3$ FIG. 3:
1/ $Pd(PPh_3)_4$, 2M $Na_2CO_3$, DME FIG. 4:
1/ $Pd(PPh_3)_4$, 2M $Na_2CO_3$, DME
2/ $^iPr_2NH$, CuI, $Pd(PPh_3)_4$
3/ BuLi, THF, −95° C.
4/ $B(OMe)_3$
5/ HCl
6/ ether, $H_2O_2$
7/ $Et_3N$, $CH_2Cl_2$, (R)-(+)-2-fluorooctan-1-ol
8/ $Et_3N$, $CH_2Cl_2$ FIG. 5:
1/ non-1-yne, $^iPr_2NH$, CuI, $[Pd(PPh_3)_4]$
2/ $H_2$, 5%Pd/C, EtOAc
3/ pent-1-yne, $^iPr_2NH$, CuI, $[Pd(PPh_3)_4]$ FIG. 6:
1/ pent-1-yne, $^iPr_2NH$, CuI, $[Pd(PPh_3)_4]$
2/ $H_2$, 5%Pd/C, EtOAc
3/ BuLi, THF, −95° C.
4/ $CO_2$
5/ DEAD, THF, $PPh_3$, (R)-2-fluorooctan-1-ol
6/ BuLi, THF, −95° C.
7/ $B(OMe)_3$
8/ HCl
9/ $H_2O_3$, ether FIG. 7:
1/ (R)-2-octanol, DEAD, THF, $PPh_3$
2/ BuLi, THF, −95° C.
3/ $Co_2$
4/ DEAD, THF, $PPh_3$, (R)-2-fluorooctan-1-ol FIG. 8:
1/ 4-hexyloxyphenylboronic acid, $Pd(PPh_3)_4$, DME, 2M $Na_2CO_3$
2/ nonyne, $^iPr_2NH$, CuI, $[Pd(PPh_3)_4]$
3/ BuLi, THF, −95° C.
5/ $H_2$, 5%Pd/C, EtOAc
6/ (R)-2-octanol, DEAD, THF, $PPh_3$
7/ 4-tetradecyloxybenzoic acid, DCC, DMA, $CH_2Cl_2$
8/ 2,3-difluoro-4-pentylphenylboronic acid, $Pd(PPh_3)_4$, DME, 2M $Na_2CO_3$ FIG. 9:
1/ $Pd(PPh_3)_4$, 2M $Na_2CO_3$, DME
2/ KF, acetamide, $Bu_4NF$
3/ Amano PS, pH 7, 1M NaOH 4/ conc $H_2SO_4$, EtOH, reflux
5/ $LiAlH_4$, THF Synthesis of 9-bromo-2-iodopyrimidine The synthetic route for the preparation of 5-bromo-2-iodopyrimidine is illustrated in more detail in FIG. 1.

The following reagents correspond to FIG. 1:
A: $Br_2/H_2O$
B: $POCl_3$
C: $HI_{(aq)}$, 0° C., mechanical shaker (or stirrer).

In FIG. 1, X may be any of the following: Cl, Br, $HSO_4$. When X=Cl, the reagent is commercially available from Aldrich. 5-bromo-2-iodopyrimidine: cold 57% hydriodic acid (281 ml, 1.25 mol) was added to a solution of 2-chloro-5-bromopyrimidine (80.6 g, 0.42 mol) (see Hird et al Liquid Crystals, 1993, 14, 741 and Brown et al Aust. J. Chem., 17, 794.) in dichloromethane (250 ml) cooled in a salt ice bath. The mixture was stirred vigourously (mechanical stirrer) at ca 0° C. for approximately 5h and carefully neutralised with solid potassium carbonate and decolourised by the addition of aqueous sodium metabisulphite solution. Water was added until all of the solids were dissolved; the organic layer was separated and the aqueous layer was extracted with dichloromethane. The combined organic solutions were dried ($Na_2CO_3$) and evaporated. Crystallisation of the crude material from light petroleum (bp 60–80° C.) gave 5-bromo-2-iodopyrimidine (99 g, 83%), mp 101–102° C. (found: C, 16.93; H, 0.62; N, 9.87; I, 44.36. $C_4H_2N_2BrI$ requires C, 16.86; H. 0.71; N, 9.83; I, 44.54%); $v_{max}/cm^{-1}$ (KBr) 3000, 1510, 1370, 1130, 1003 and 622; delta (270 MHz; $CDCl_3$) 8.54 (2H, s), m/z 286 ($M^+$), 284 ($M^+$), 259 ($M^+$−HCN), 257 ($M^+$−HCN). 194, 192, 178, 159, 157 and 127.

It is also possible to incorporate a co-solvent for the synthesis of 2-iodo-5-bromopyrimidine, such a solvent might be a chlorinated solvent such as dichloromethane or chloroform, alternatively it might be a hydrocarbon.

The suitability of compound I for the synthesis of a number of known liquid crystal compounds was tested:

EXAMPLE 1

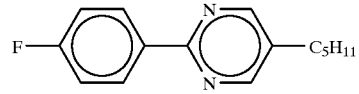

The scheme for the synthesis of this compound is illustrated in FIGS. 3 and 5. The following reagents correspond to the steps in FIG. 3:
2: $[Pd(PPh_3)_4]$, 2M $Na_2CO_3$, DME
The following reagents correspond to the steps in FIG. 5:
3: pent-1-yne, $^iPr_2NH$, CuI, $[Pd(PPh_3)_4]$
2: $H_2$, 5%Pd/C, EtOAc

EXAMPLE 2

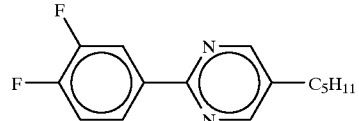

The scheme for the synthesis of this compound is illustrated in FIGS. 2 and 6. The following reagents correspond to the steps in FIG. 2:

2: [Pd(PPh)₄], 2M Na₂CO₃, DME
The following reagents correspond to the steps in FIG. 6:
1: pent-1-yne, ⁱPr₂NH, CuI, [Pd(PPh₃)₄]
2: H₂, Pd/C, EtOAc

EXAMPLE 3

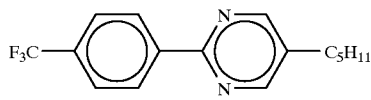

The scheme for the synthesis of this compound is illustrated in FIGS. 2 and 5. The following reagents correspond to the steps in FIG. 2:
2: [Pd(PPh₃)₄], 2M Na₂CO₃, DME
The following reagents correspond to the steps in FIG. 5:
3: pent-1-yne, ⁱPr₂NH, CuI, [Pd(PPh₃)₄]
2: H₂, 5%Pd/C, EtOAc

EXAMPLE 4

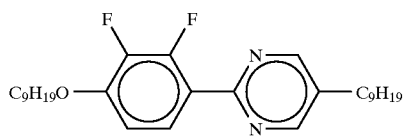

The scheme for the synthesis of this compound is illustrated in FIGS. 2 and 5. The following reagents correspond to the steps in FIG. 2:
2: [Pd(PPh₃)₄], 2M Na₂CO₃, DME The following reagents correspond to the steps in FIG. 5:
1: nonyne, ⁱPr₂NH, CuI, [Pd(PPh₃)₄]
2: H₂, 5%Pd/C, EtOAc The current invention also describes the synthesis of compounds which are believed to be novel.

EXAMPLE 1

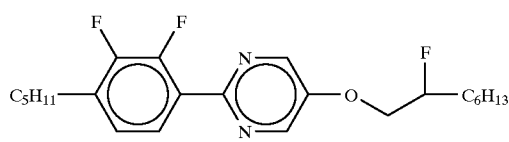

The scheme for the synthesis of this compound is illustrated in FIGS. 3 and 4. The following reagents correspond to the steps in FIG. 3:
1: Pd(PPh₃)₄, DME, 2M Na₂CO₃
The following reagents correspond to the steps in FIG. 4:
3: BuLi, THF, −95° C.
4: B(OMe)₃
5: HCl
6: ether, H₂O₂
7: Et₃N, CH₂Cl₂, (R)-(+)-2-fluorooctan-i-ol

EXAMPLE 2

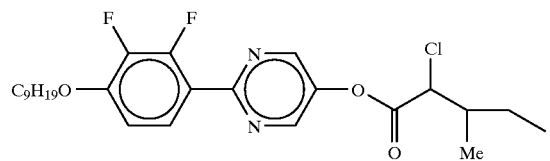

The scheme for the synthesis of this compound is illustrated in FIGS. 2 and 4. The following reagents correspond to the steps in FIG. 2:

1: Pd(PPh₃)₄, DME, 2M Na₂CO₃
The following reagents correspond to the steps in FIG. 4:
3: BuLi, THF, −95° C.
4: B(OMe)₃
5: HCl
6: ether, H₂O₂
8: Et₃N, CH₂Cl₂

EXAMPLE 3

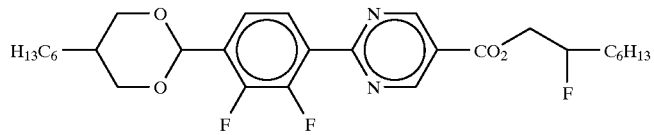

The scheme for the synthesis of this compound is illustrated in FIGS. 3 and 7. The following reagents correspond to the steps in FIG. 3:

1: Pd(PPh₃)₄, DME, 2M Na₂CO₃
The following reagents correspond to the steps in FIG. 7:
2: BuLi −95° C., THF
3: CO₂
4: DEAD, PPh₃, (R)-2-fluorooctanol, THF

EXAMPLE 4

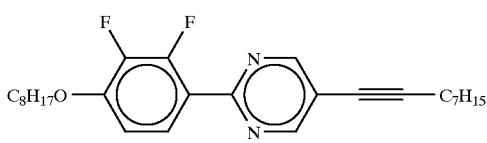

The scheme for the synthesis of this compound is illustrated in FIGS. 2 and 5. The following reagents correspond to the steps in FIG. 2:

2: [Pd(PPh$_3$)$_4$], 2M Na$_2$Co$_3$, DME

The following reagents correspond to the steps in FIG. 5:

1: non-1-yne, $^i$Pr$_2$NH, CuI, [Pd(PPh$_3$)$_4$]

EXAMPLE 5

F$_3$C—⟨phenyl⟩—⟨pyrimidine⟩—≡—C$_3$H$_7$

The scheme for the synthesis of this compound is illustrated in FIGS. 2 and 5. The following reagents correspond to the steps in FIG. 2:

2: [Pd(PPh$_3$)$_4$], 2M Na$_2$CO$_3$, DME

The following reagents correspond to the steps in FIG. 5:

3: pent-1-yne, $^i$Pr$_2$NH, CuI, [Pd(PPh$_3$)$_4$]

EXAMPLE 6

F—⟨phenyl⟩—⟨pyrimidine⟩—≡—C$_3$H$_7$

The scheme for the synthesis of this compound is illustrated in FIGS. 3 and 5. The following reagents correspond to the steps in FIG. 3:

2: [Pd(PPh$_3$)$_4$], 2M Na$_2$CO$_3$, DME

The following reagents correspond to the steps in FIG. 5:

3: pent-1-yne, $^i$Pr$_2$NH, CuI, [Pd(PPh$_3$)$_4$]

EXAMPLE 7

F,F—⟨phenyl⟩—⟨pyrimidine⟩—≡—C$_3$H$_7$

The scheme for the synthesis of this compound is illustrated in FIGS. 2 and 6. The following reagents correspond to the steps in FIG. 2:

2: [Pd(PPh$_3$)$_4$], 2M Na$_2$CO$_3$, DME

The following reagents correspond to the steps in FIG. 6:

1: pent-1-yne, $^i$Pr$_2$NH, CuI, [Pd(PPh$_3$)$_4$]

EXAMPLE 8

H$_7$C$_3$—⟨cyclohexyl⟩—⟨phenyl(F,F)⟩—⟨pyrimidine⟩—CO$_2$—CH$_2$CH(F)—C$_3$H$_7$ The scheme for the synthesis of this compound is illustrated in FIGS. 3 and 7. The following reagents correspond to the steps in FIG. 3:

1: Pd(PPh$_3$)$_4$, DME, 2M Na$_2$CO$_3$

The following reagents correspond to the steps in FIG. 7:

2: BuLi −95° C., THF
3: CO$_2$
4: DEAD, PPh$_3$, (R)-2-fluorooctanol, THF

EXAMPLE 9

C$_8$H$_{17}$O—⟨phenyl⟩—≡—⟨pyrimidine⟩—⟨phenyl⟩—OC$_6$H$_{13}$

The scheme for the synthesis of this compound is illustrated in FIGS. 4 and 8. The following reagents correspond to the steps in FIG. 4:

1: $^i$Pr$_2$NH, CuI, [Pd(PPh$_3$)$_4$]

The following reagents correspond to the steps in FIG. 8:

1: 4-hexyloxyphenylboronic acid, Pd(PPh$_3$)$_4$, DME, 2M Na$_2$CO$_3$

EXAMPLE 10

C$_8$H$_{17}$O—⟨phenyl⟩—≡—⟨pyrimidine⟩—≡—C$_7$H$_{15}$

The scheme for the synthesis of this compound is illustrated in FIGS. 4 and 8. The following reagents correspond to the steps in FIG. 4:

1: $^i$Pr$_2$NH, CuI, [Pd(PPh$_3$)$_4$]

The following reagents correspond to the steps in FIG. 8:

2: 1-nonyne, CuI, Pd(PPh$_3$)$_4$, diisopropylamine.

EXAMPLE 11

C$_{14}$H$_{29}$O—⟨phenyl⟩—CO$_2$—⟨phenyl⟩—⟨pyrimidine⟩—C(O)O—CH(Me)—C$_6$H$_{13}$ The scheme for the synthesis of this compound is illustrated in FIGS. 3 and 8. The following reagents correspond to the steps in FIG. 3:

1: Pd(PPh$_3$)$_4$, DME, 2M Na$_2$CO$_3$

The following reagents correspond to the steps in FIG. 8:

3: BuLi −95° C., THF
4: CO$_2$

5: H$_2$, 5%Pd/C, EtOAc
6: (R)-2-octanol, DEAD, THF, PPh$_3$
7: 4-tetradecyloxybenzoic acid, DCC, DMA, CH$_2$Cl$_2$

EXAMPLE 12

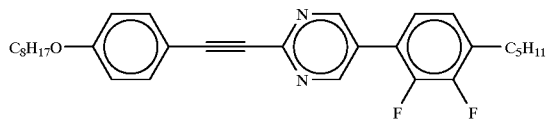

The scheme for the synthesis of this compound is illustrated in FIGS. 4 and 8. The following reagents correspond to the steps in FIG. 4:
1: $^i$Pr$_2$NH, CuI, [Pd(PPh$_3$)$_4$]
The following reagents correspond to the steps in FIG. 8:
8: 2,3-difluoro-4-pentylphenylboronic acid, Pd(PPh$_3$)$_4$, DME, 2M Na$_2$CO$_3$

EXAMPLE 13

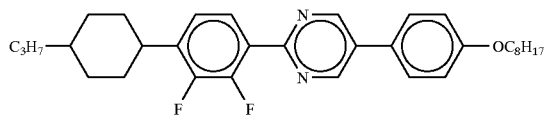

The scheme for the synthesis of this compound is illustrated in FIGS. 3 and 9. The following reagents correspond to the steps in FIG. 3:
1: Pd(PPh$_3$)$_4$, DME, 2M Na$_2$CO$_3$
The following reagents correspond to the steps in FIG. 9:
1: Pd(PPh$_3$)$_4$, DME, 2M Na$_2$CO$_3$
The compound of formula I may also be used to synthesise the compounds described in UK patent application GB 9413324.6.

Experimental

Melting points and liquid crystal transition temperatures were measured using a Mettler FP5 hot-stage and control unit in conjunction with an Olympus BH2 polarising microscope. These were confirmed by differential scanning calorimetry (DSC) carried out on a Perkin Elmer DSC 7 with TAC 7/PC instrument interface and controlled cooling accessory. Heating and cooling rates were between 5 and 20° C. min$^{-1}$. A nitrogen atmosphere was maintained in the furnace. The reference sample was gold and the calibration sample was indium. Analytical thin-layer chromatography (TLC) was performed on Kieselgel silica gel 60 F254, backed onto aluminium sheets, and spots were visualised with UV light and iodine. The progress of reactions was often monitored using a Perkin Elmer 8310 capillary gas chromatograph fitted with a 12 m QC2/BP1–1.0 SGE column (N$_2$ carrier) and a flame ionisation detector. Purity of compounds was checked by high performance liquid chromatography (HPLC) on a Lichrocart 125-4 Superspher RP18 column connected to a Merck-Hitachi L4000 UV detector, L 6200A pump, D-6000 interface and D-6000 HPLC manager eluting with chloroform/acetonitrile. Optical rotations were measured using an ETL-NPL Automatic Polarimeter Control Unit Type 143A at the sodium D line (λ=589 nm) and at the temperature reported, concentration (c g/100 ml). Infrared (IR) spectra were obtained using either a Perkin Elmer 983G or a Perkin Elmer 487G spectrometer (s=strong, sh=shoulder) as thin films or potassium bromide discs. $^1$H NMR spectra were recorded on a JEOL JMN GX270 FT spectrometer (270 MHz) in deuteriochloroform unless otherwise stated. Chemical shifts are reported in ppm from an internal standard of TMS. Selected data are reported as follows: chemical shift, multiplicity (s=singlet, d=doublet, t=triplet, q=quartet, m=multiplet, br=broad), coupling constant (hertz) and assignment. Mass spectra were recorded on a Finnigan MAT 1020 GC/MS spectrometer; M$^+$ represents the molecular ion. The syringe pump employed in enzymatic hydrolyses was a Razel A-99 model. Flash chromatography was carried out using Sorbsil C60 (40–60 μm) grade silica. THF was freshly distilled from potassium/benzophenone ketyl, AnalaR ether was dried over sodium wire and dry dichloromethane was distilled from calcium hydride. Light petroleum refers to the fraction (b.p. 40–60° C.) unless otherwise stated. 0.063M Phosphate buffer solution (pH 7) was prepared by the addition of 0.1M sodium hydroxide solution (291 ml) to 0.1M potassium dihydrogen phosphate solution (500 ml). Cooling to ca. −95° C. was achieved using a liquid nitrogen-industrial methylated spirit slush bath. The enzymic resolution was carried out using a similar procedure (P. Kaiartis and R. W. Regenye, Org. Synth., 69, 10) to that described for ethyl 2-fluorohexanoate. A sample of the enzyme Pseudomonas lipase PS (previously denoted as P-30) was kindly donated by Amano Enzyme Europe Ltd. Boronic acids were prepared by lithiation of aryl bromides and by fluoro-directed ortho-lithiation using methods as previously described (M. Hird, G. W. Gray and K. J. Toyne, Liquid Crystals, 1992, 11, 531; G. W. Gray, M. Hird. D. Lacey, and K. J. Toyne, J Chem. Soc., Perkin Trans. II, 1989, 2041). (2S, 3S)-2-Chloro-3-methylpentanoyl chloride was prepared from the corresponding acid by the addition of 1 drop of DMF to a solution of the acid (S. J. Fu, S. M. Birnbaum and J. P. Greenstein, J. Am. Chem. Soc., 1954, 76, 6054) and oxalyl chloride (1.2 equiv.) in dry dichloromethane. 57% Hydriodic acid was purchased from Janssen Chimica (now Acros Chimica) and was unstabilised. Tetrabutylammonium fluoride was purchased from Aldrich as a 1M solution in THF and was used as supplied.

5-Bromo-2-iodopyrimidine 2.—Cold 57% hydriodic acid (281 ml, 1.25 mol) was added to a solution of 5-bromo-2-chloropyrimidine (D. J. Brown and J. M. Lyall, Aust. J Chem., 1964, 17, 794) 1 (80.6 g, 0.42 mol) in dichloromethane (250 ml) cooled in a salt-ice bath. The mixture was stirred vigorously (mechanical stirrer) at ca. 0° C. for 5 h and carefully neutralised with solid potassium carbonate and decolourised by the addition of aqueous sodium metabisulfite solution. Water was added until all the solids were dissolved; the organic layer was separated and the aqueous layer was extracted with dichloromethane. The combined organic solutions were dried (Na$_2$CO$_3$) and evaporated. Crystallisation of the crude material from light petroleum (b.p. 60–80° C.) gave 5-bromo-2-iodopyrimidine 2 (99 g, 83%), m.p. 101–102 ° C (Found: C: 16.93; H, 0.62. N, 9.87; I, 44.36. C$_4$H$_2$N$_2$BrI requires C, 16.86; H, 0.71. N, 9.83; I, 44.54%); ν$_{max}$/cm$^{-1}$(KBr) 3000, 1510, 1370, 1130, 1003, and 622; δ 8.54 (s); m/z 286 (M$^+$), 284 (M$^+$), 259 (M$^+$−HCN), 257 (M$^+$−HCN), 194, 192, 178, 159, 157 and 127.

2-(2',3'-Difluoro-4'-octyloxyphenyl)-5-bromopyrimidine 4.—To a degassed mixture of 5-bromo-2-iodopyrimidine 2 (4.0 g, 14.0 mmol), tetrakis(triphenylphosphine)palladium (323 mg, 0.28 mmol), DME (30 ml), and aqueous 2M sodium carbonate (50 ml) was added 2,3-difluoro-4-octyloxyphenylboronic acid 3 (4.42 g, 15.4 mmol) dropwise in DME (10 ml) under an atmosphere of nitrogen. The mixture was heated under reflux overnight; water was added to the mixture and the organic layer was separated. The aqueous layer was extracted with ethyl acetate (twice) and the combined organic solutions were washed with brine and dried (MgSO$_4$). The solvent was removed in vacuo and the residue was purified by flash chromatography (5% to 10% ethyl acetate-light petroleum; the crude material was preloaded onto silica in dichloromethane) to give the phenylpyrimidine 4 (3.1 g, 55%) (from methanol), m.p. 74.6° C.; $v_{max}$/cm$^{-1}$(KBr) 2920, 2850, 1625, 1475, 1420, 1310 and 1090; δ 0.91(1H, t, Me), 1.2–1.55(10H, m), 1.85 (2H, quint. OCH$_2$CH$_2$), 4.11 (2H, t, OCH$_2$), 6.82 (1H, ddd, 5'-H), 7.83 (1H, ddd, 6'-H) and 8.86 (2H, s, 4- and 6-H); m/z 288 (M$^+$–C$_8$H$_{16}$), 286 (M$^+$–C$_8$H$_{16}$), 178 and 155.

2-(2'-Fluoro-4'-octyloxyphenyl)-5-bromopyrimidine 6.—Quantities: 5-bromo-2-iodopyrimidine 2 (4.05 g, 14.2 mmol), 2-fluoro-4-octyloxyphenylboronic acid 5 (4.57 g, 17.0 mmol), tetrakis(triphenylphosphine)palladium (328 mg, 0.28 mmol), 2M sodium carbonate (50 ml), DME (50 ml). The experimental procedure was as described for compound 4 to yield the monofluorophenylpyrimidine 6 (3.68 g, 69%) (from MeOH), m.p. 71.6° C.; $v_{max}$/cm$^{-1}$(KBr) 2920, 2850, 1610, 1410, 1270, 1125 and 830; δ 0.90 (3H, t, Me), 1.20–1.55 (10H, m), 1.82 (2H, quint, OCH$_2$CH$_2$), 4.00 (2H, t, OCH$_2$), 6.75 (2H, m, 3'- and 4'-H), 8.06 (1H, t, 6'-H) and 8.85 (2H, s, 4- and 6-H); m/z 382 (M$^+$), 380 (M$^+$), 270 (M$^+$–C$_8$H$_{16}$), 268 (M$^+$–C$_8$H$_{16}$) and 137.

2-(4'-Octyloxyphenyl)-5-bromopyrimidine 8.—Quantities: 5-bromo-2-iodopyrimidine 2 (1.23 g, 4.32 mmol), 4-octyloxyphenylboronic acid 7 (1.33 g, 5.18 mmol), tetrakis(triphenylphosphine)palladium (150 mg, 0.13 mmol), DME (30 ml), aqueous 2M sodium carbonate (30 ml). The experimental procedure was as described for compound 4 to yield the phenylpyrimidine 8 (0.67 g, 43%) (from EtOH), m.p. 95.0° C.; $v_{max}$/cm$^{-1}$(KBr) 2920, 1605, 1525, 1425, 1260, 1170, 1120 and 790; δ 0.90 (3H, t, Me), 1.20–1.55 (10H, m), 1.84 (2H, quint, OCH$_2$CH$_2$), 4.02 (2H, t, OCH$_2$), 6.97 (2H, d, J 7, 3'- and 5'-H), 8.33 (2H, d, J 7, 2'- and 6'-H) and 8.76 (2H, s, 4- and 6-H); m/z 366 (M$^+$), 364 (M$^+$), 252 (M$^+$–C$_8$H$_{16}$) 250 (M$^+$–C$_8$H$_{16}$), 195 and 186.

2-[4'-(Trifluoromethyl)phenyl]-5-bromopyrimidine 10.—Quantities: 5-bromo-2-iodopyrimidine 2 (2.64 g, 9.26 mmol), 4-(trifluoromethyl)phenylboronic acid 9 (2.29 g, 12.0 mmol), tetrakis(triphenylphosphine)palladium (53 mg, 0.046 mmol), DME (50 ml), 2M aqueous sodium carbonate (50 ml). The experimental procedure was as described for compound 4 to yield the trifluoromethylphenylpyrimidine 10 (1.58 g, 56%) (from MeOH), m.p. 167° C.; $v_{max}$/cm$^{-1}$ (KBr) 1530, 1420, 1320s, 1165, 1120, 1070 and 1010; δ 7.74 (2H, d, J 8, 3'- and 5'-H), 8.52 (2H, d, J 8, 2'- and 6'-H) and 8.86 (2H, s, 4- and 6-H); m/z 304 (M$^+$), 302 (M$^+$), 196 and 171.

2-(3',4'-Difluorophenyl)-5-bromopyrimidine 12.—Quantities: 5-bromo-2-iodopyrimidine 2 (3.84 g, 14.9 mmol), 3,4-difluorophenylboronic acid (3.06 g, 19.4 mmol), tetrakis(triphenylphosphine)palladium (344 mg, 0.30 mmol), DME (50 ml), aqueous 2M sodium carbonate (50 ml). The experimental procedure was as described for compound 4. The crude product was purified by flash chromatography (5% ethyl acetate-light petroleum) to give the difluorophenylpyrimidine 12 (3.97 g, 75%) (from MeOH), m.p. 148° C.; $v_{max}$/cm$^{-1}$ 1610, 1530, 1435s, 1330, 1270, 790 and 780; δ 7.26(1H, m, 5'-H), 8.17–8.30(2H, m, 2' and 6'-H) and 8.82 (2H, s,4- and 6-H); m/z 272 (M$^+$), 270 (M$^+$), 164 and 139.

2-(4'-Cyanophenyl)-5-bromopyrimidine 14.—Quantities: 5-bromo-2-iodopyrimidine 2 (2.50 g, 8.77 mmol), 4-cyanophenylboronic acid 13 (1.42 g, 9.65 mmol), tetrakis (triphenylphosphine)palladium (304 mg, 0.26 mmol), DME (50 ml), aqueous 2M sodium carbonate (50 ml). The experimental procedure was as described for compound 4 to yield the cyanophenylpyrimidine 14 (1.85 g, 81%) (from MeOH), m.p. 222° C.; $v_{max}$/cm$^{-1}$(KBr) 2200 (CN), 1520, 1420s, 1120, 1015, 860 and 790; δ 7.76 (2H, d, 3'- and 5'-H), 8.54 (2H, d, 2'- and 6'-H) and 8.83 (2H, s, 4- and 6-H); m/z 261 (M$^+$), 259 (M$^+$), 234 (M$^+$–HCN), 232 (M$^+$–HCN), 153 and 128.

2-[2',3'-Difluoro-4'-(trans-pentylcyclohexylethyl) phenyl]-5-bromopyrimidine 16.—Quantities: 5-bromo-2-iodopyrimidine 2 (2.49 g, 8.74 mmol), 2,3-difluoro-4-(trans-4'-pentylcyclohexylethyl)phenylboronic acid 15 (3.54 g, 10.5 mmol), tetrakis(triphenylphosphine)palladium (303 mg, 0.26 mmol), DME (30 ml), 2M aqueous sodium carbonate (30 ml). The experimental procedure was as described for compound 4 to yield the cyclohexylethylphenylpyrimidine 16 (3.88 g, 98%) (from EtOH), transitions/° C. K 128.5N 138.5 I; $v_{max}$/cm$^{-1}$(KBr) 2920, 2840, 1530, 1460, 1420s, 1010 and 900; δ 0.80–1.05 (7H, m), 1.08–1.40 (10H, m), 1.54 (2H, quint), 1.75 (4H, m), 2.70 (2H, t), 7.04 (1H, ddd, 5'-H), 7.74 (1H, ddd, 6'-H) and 8.89 (2H, s, 4- and 6-H); m/z 452 (M$^+$), 450 (M$^+$), 286. 284, 172 and 170.

2-[2',3'-Difluoro-4'-(trans-5"-yl)hexyl-1",3"-dioxan-2"-yl)phenyl]-5-bromopyrimidine Quantities: 5-bromo-2-iodopyrimidine 2 (3.12 g, 10.9 mmol), 2',3'-difluoro-4'-(trans-5"-hexyl-1",3"-dioxan-2"-yl)phenylboronic acid 17 (4.30 g, 13.1 mmol), tetrakis(triphenylphosphine)palladium (252 mg, 0.22 mmol), DME (50 ml), aqueous 2M sodium carbonate (50 ml). The experimental procedure was as described for compound 4. The cooled reaction mixture was partitioned in ether-water and the aqueous layer was washed with dichloromethane (twice). The combined organic solutions were washed with brine, dried (Na$_2$CO$_3$) and evaporated. The residue was purified by flash chromatography (5 to 10% ethyl acetate-light petroleum; the crude material was preloaded onto silica in dichloromethane) to give the pyrimidine 18 (1.55 g, 32%) (from EtOH), m.p. 110–112° C.; $v_{max}$/cm$^{-1}$(KBr) 2920, 2850, 1530, 1460s, 1420s, 1390s, 1130, 1020, 1010 and 795, δ 0.87 (3H, t, Me), 1.11 (2H, m), 1.23–1.35 (8H, m) 2.17 (1H, m, 4"-H), 3.58 (2H, t, J 12, 4"$_{ax}$- and 6"$_{ax}$-H), 4.25 (2H, dd, J$_{gem}$ 12 and J$_{vic}$ 5, 4" eq.- and 6" eq.-H), 5.75 (1H, s, 2"-H), 7.49 (1H, ddd, J 8, 7 and 2, 6'-H), 7.88 (1H ddd, J 8, 7 and 2, 5'-H) and 8.91 (2H, s, 4- and 6-H); m/z 442'(M$^+$), 440 (M$^+$), 299, 297, 166 and 107.

2-(4'-Fluorophenyl)-5-bromopyrimidine 20.—Quantities: 5-bromo-2-iodopyrimidine 2 (4.00 g, 14.0 mmol), 4-fluorophenylboronic acid 19 (2.44 g, 17.4 mmol), tetrakis (triphenylphosphine)palladium (324 mg, 0.28 mmol), DME (50 ml), aqueous 2M sodium carbonate (50 ml). The experimental procedure was as described for compound 4. The crude product was purified by flash chromatography (5% ethyl acetate-light petroleum) to give the fluorophenylpyrimidine 20 (3.3 g, 94%) (from MeOH), m.p. 155.5° C.; $v_{max}$/cm$^{-1}$(KBr) 1595, 1525, 1505, 1400s, 1220, 1150 and 785; δ 7.15 (2H, dd, J9, 3'- and 5'-H), 8.41 (2H, dd, J9 and 4, 2'- and 6'-H) and 8.80 (2H, s, 4- and 6-H); m/z 254 (M$^+$), 252 (M$^+$), 227 (M$^+$–HCN), 225 (M$^+$–HCN), 146 and 121.

2-[2',3'-Difluoro4'-(cis/trans-4"-propylcyclohexy) phenyl]-5-bromopyrimidine 22.—Quantities: 5-bromo-2-iodopyrimidine 2 (2.49 g, 8.74 mmol), 2,3-difluoro-4-(cis/trans-4'-propylcyclohexyl)phenylboronic acid 21 (3.54 g, 10.5 mmol), tetrakis(triphenylphosphine)palladium (303 mg, 0.26 mmol), DME (30 ml), 2M aqueous sodium carbonate (30 ml). The experimental procedure was as described for compound 4 to yield the cis/trans-cyclohexylphenylpyrimidine 22 (6.36 g, 87%) (from MeOH/EtOH) in a ratio of isomers (1.6:1) as determined by HPLC); $v_{max}/cm^{-1}$(KBr) 2920, 2850, 1625, 1587, 1455, 1420, 1370, 1330, 1110, 1010 and 900, δ 0.90 (3H, t, Me), 1.03–2.00(13H, m), 2.94 (1H, m, ArCH), 7.10 (1H, m, 5'-H), 7.67 (1H, m, 6'-H) and 8.89 (2H, s, 4- and 6-H); m/z 396 ($M^+$), 394 ($M^+$), 378, 376, 354 ($M^+-C_3H_6$), 352 ($M^+-C_3H_6$), 313, 311, 298, 296, 285 and 283.

2-(2',3'-Difluoro-4'-pentylphenyl)-5-bromopyrimidine 24.—Quantities: 5-bromo-2-iodopyrimidine 2 (6.26 g, 22.0 mmol), 2,3-difluoro-4-pentylphenylboronic acid 23 (5.51 g, 24.2 mmol), tetrakis(triphenylphosphine)palladium (508 mg, 0.44 mmol), 2M sodium carbonate (60 ml), DME (60 ml). The experimental procedure was as described for compound 4. Flash chromatography of the crude product (3 to 4% ethyl acetate-light petroleum) gave the difluoropentylphenyl-pyrimidine 24 (3.43 g, 45%) (from MeOH), m.p. 73.3° C., $v_{max}/cm^{-1}$(KBr) 2920, 2860, 1625, 1530, 1460s, 1420s, 1370, 905 and 785; δ 0.90 (3H, t, Me), 1.35 (4H, m), 1.65 (2H, m, ArCH$_2$CH$_2$), 2.70 (2H, t, ArCH$_2$), 7.06 (1H, ddd, 5'-H), 7.74 (1H, ddd, 6'-H) and 8.88 (2H, s, 4- and 6-H); m/z 342 ($M^+$), 340 ($M^+$), 285 ($M^+$-C$_4$H$_9$), 283 ($M^+$-C$_4$H$_9$), 152, 125 and 108.

2-(4'-Benzyloxyphenyl)-5-bromopyrimidine 26.—Quantities: 5-bromo-2-iodopyrimidine 2 (4.33 g, 15.2 mmol), 4-benzyloxyphenylboronic acid 25 (3.81 g, 16.7 mmol), tetrakis(triphenylphosphine)palladium (351 mg, 0.30 mmol), 2M sodium carbonate (50 ml), DME (50 ml). The experimental procedure was as described for compound 4 to yield the benzyloxyphenylpyrimidine 26 (4.12 g, 79%) (from EtOH), m.p. 155° C.; $v_{max}/cm^{-1}$(KBr) 3200, 1600, 1550, 1520, 1410, 1325, 1250, 1165, 1040, 1025, 1010 and 840; δ 5.14 (2H, s, OCH$_2$), 7.06 (2H, d, J 9, 3'- and 5'-H), 7.30–7.48 (5H, m, PhH), 8.35 (2H, d, J 9, 2'-and 6'-H) and 8.77 (2H, s, 4- and 6-H); m/z 342 ($M^+$), 340 ($M^+$), 249, 221, 196, 142, 115 and 91.

2-(2'-Fluoro-4'-benzyloxyphenyl)-5-bromopyrimidine 28.—Quantities: 5-bromo-2-iodopyrimidine 2 (5.05 g, 17.7 mmol), 2-fluoro-4-benzyloxyphenylboronic acid 27 (4.84 g, 19.7 mmol), tetrakis(triphenylphosphine)palladium (680 mg, 0.59 mmol), 2M sodium carbonate (50 ml), DME (50 ml). The experimental procedure was as described for compound 4 to yield the benzyloxyfluorophenylpyrimidine 28 (3.34 g, 53%) (from MeOH), m.p. 124.2° C.; $v_{max}/cm^{-1}$(KBr) 3030, 2860, 1615s, 1430, 1420, 1320, 1215, 1020 and 830, δ 5.22 (2H, s, CH$_2$), 6.75–6.89 (2H, m, 3'- and 5'-H), 7.32–7.48 (5H, m, Ph), 8.06 (1H, t, 6'-H) and 8.85 (2H, s, 4-and 6-H); m/z 360 ($M^+$), 358 ($M^+$), 269 ($M^+$–PhCH$_2$), 267 ($M^+$–PhCH$_2$), 247, 221 and 91.

2-(4'-Pentylphenyl)-5-bromopyrimidine 30.—Quantities: 5-bromo-2-iodopyrimidine 2 (14.4 g, 50.4 mmol), 4-pentylphenylboronic acid 29 (10.65 g, 55.4 mmol), tetrakis(triphenylphosphine)palladium (1.70 g, 1.47 mmol), 2M sodium carbonate (100 ml), DME (100 ml). The experimental procedure was as described for compound 4. Flash chromatography of the crude product (3 to 5% ethyl acetate-light petroleum) gave the pentylphenylpyrimidine 30 (8.50 g, 55%) (from MeOH). m.p. 82.7° C.; $v_{max/cm}^{-1}$(KBr) 2920, 1605, 1530, 1425s, 1370, 1120, 1015 and 785; δ 0.89 (3H, t, Me), 1.34 (4H, m), 1.65 (2H, quint, ArCH$_2$CH$_2$), 2.66 (2H, t, ArCH$_2$), 7.28 (2H, d, 3'- and 5'-H), 8.29 (2H, d, 2'- and 6'-H), 8.75 (2H, s, 4- and 6-H); m. 306 ($M^+$), 304 ($M^+$), 263 ($M^+-C_3H_7$), 261 ($M^+-C_3H_7$), 249 ($M^+-C_4H_9$), 247 ($M^+-C_4H_9$), 168 and 116.

1-(4'-Octyloxyphenyl)-2-(5''-bromopyrimidin-2''-yl) ethyne 32.—A degassed mixture of 4'-octyloxyphenylethyne 31 (4.95 g, 21.5 mmol), 5-bromo-2-iodopyrimidine 2 (5.83 g, 20.4 mmol), tetrakis (triphenylphosphine)palladium (1.24 g, 1.07 mmol) and copper(I) iodide (205 mg, 1.07 mmol) in diisopropylamine (60 ml) was heated under reflux for 2 h. The solvent was removed in vacuo and the residue was purified by flash chromatography (5% ethyl acetate-light petroleum, the residue was preloaded onto silica in dichloromethane) to give the tolane 32 (4.44 g, 56%) [from toluene-light petroleum (b.p. 60–80° C.)], m.p. 138.2° C.; $v_{max}/cm^{-1}$(KBr) 2920, 2850. 2220, 2190, 1600, 1505s, 1250, 1170 and 835; δ 0.90 (3H t, Me), 1.20–1.52 (10H, m), 1.75 (2H, quint, OCH$_2$CH$_2$), 3.97(2H, t, OCH$_2$), 6.88 (2H, d, 3'- and 5'-H), 7.60 (2H, d, 2'- and 6'-H) and 8.77 (2H, s, 4''- and 6''-H); m/z 388 ($M^+$), 386 ($M^+$), 276 ($M^+-C_8H_{16}$), 274 ($M^+-C_8H_{16}$) and 143.

2-(2',3'-Difluoro-4'-pentylphenyl)-5-hydroxypyrimidine 33.—1.6M Butyllithium (4 ml, 6.48 mmol) was added dropwise to a solution of 2-(2',3'-difluoro-4'-pentylphenyl)-5-bromopyrimidine 24 (2.01 g. 5.89 mmol) in THF (60 ml) and dry hexane (10 ml) with stirring under nitrogen at –95° C. The solution was maintained below –90° C. for 45 min and trimethylborate (1.25 ml, 11.0 mmol) in THF (5 ml) was added dropwise at such a rate to maintain the temperature below –90° C. The mixture was allowed to warm to ambient temperature overnight with the cooling bath in place. Saturated ammonium chloride solution was added and stirring was continued for 1 h. The product was extracted into ether (twice) and the combined ethereal extracts were washed with brine, dried (MgSO$_4$) and the solvent was removed in vacuo. The residue was dissolved in ether (50 ml) and 30% hydrogen peroxide (2.7 ml, 23.6 mmol) was added. The mixture was heated under reflux for 6 h. A saturated solution of sodium sulphite was added dropwise with stirring to the ice cooled mixture until the vigorous reaction ceased. The organic layer was separated and the aqueous layer was extracted with ether (twice). The combined organic solutions were washed with brine, dried (MgSO$_4$) and evaporated. Flash chromatography (5% ethyl acetate-light petroleum, the residue was adsorbed onto silica in dichloromethane) gave the hydroxypyrimidine 33 (736 mg, 40%) [from light petroleum (b.p. 60–80° C.)-toluene], m.p. 104–105° C.; $v_{max}/cm^{-1}$(KBr) 3080br (OH), 2930, 1555, 1465, 1420, 1285, 1180 and 900; δ 0.90 (3H, t, Me), 1.33 (4H, m),1.62 (2H, quint, ArCH$_2$CH$_2$), 2.69 (2H, t, ArCH$_2$), 7.03 (1H, dt, 5'-H), 7.60 (1H, dt, 6'-H), 8.42 (2H, s, 4- and 6-H) and 8.97 (1H, br s, OH), m/z 278 ($M^+$), 235 ($M^+-C_3H_7$), 222, 221, 166, 152 and 125.

(R)-(–)-2-(2',3'-Difluoro-4'-pentylphenyl)-5-(2-fluorooctyloxy)pyrimidine 34.—DEAD (470 mg, 2.70 mmol) in THF (3 ml) was added dropwise via syringe to a stirring solution of (R)-(+)-2-fluorooctanol (396 mg, 2.70 mmol), the hydroxypyrimidine 33 (750 mg, 2.70 mmol) and triphenylphosphine (707 mg, 2.70 mmol) in THF (10 ml) under nitrogen at ambient temperature for 15 h. The solvent was removed in vacuo and the residue was purified by flash chromatography (3 to 5% ethyl acetate-light petroleum) to give the 2-fluorooctyloxypyrimidine 34 (610 mg, 55%) (from MeOH), m.p. 74.7° C.; $[\alpha]_D^{25}$ –3.6° (c 2.7 in CHCl$_3$); $v_{max}/cm^{-1}$(KBr) 2950, 2920, 1575, 1545, 1460, 1440, 1280, 1210, 1130, 1080 and 995; δ 0.90 (6H, overlapping t, Me), 1.26–1.93 (16H, m), 2.70 (2H, t, ArCH$_2$), 4.22 (2H, dd, $^3J_{HF}$ 22 and J$_{vic}$ 4, OCH$_2$), 4.87 (1H, d of sext, $^2J_{HF}$ 49 and J4, CHF), 7.02 (1H ddd, J7.5, 7 and 2, 5'-H), 7.6 (1H, ddd, J7.5, 7 and 2, 6'-H) and 8.55 (2H, s, 4- and 6-H); m/z 408 ($M^+$), 365, 351, 291, 278, 250 and 221.

2-(2',3'-Difluoro-4'-octyloxyphenyl)-5-hydroxypyrimidine 35.—Quantities: difluorophenylbromopyrimidine 4 (4.30 g, 10.8 mmol), 2.5M butyllithium (4.5 ml, 11.3 mmol), trimethyl borate (2.6 ml, 22.6 mmol), THF (100 ml), hexane (30 ml), 30% hydrogen peroxide (5.4 ml, 44 mmol) ether (200 ml). The experimental procedure was as described for compound 33. The crude product was purified by flash chromatography (10 to 30% ethyl acetate-light petroleum) to give the difluorophenyl-5-hydroxypyrimidine 35 (2.04 g, 56%) [from light petroleum (b.p. 60–80° C.)], m.p. 84–85° C.; $v_{max}$/cm$^{-1}$(KBr) 3 100br, 2920, 2850, 1620, 1560, 1510, 1475, 1430, 1300, 1285, 1200 and 1085; δ 0.91 (3H, t, Me), 1.19–1.52 (10H, m), 1.32 (2H, quint, OCH$_2$CH$_2$), 4.05(2H, t, OCH$_2$), 6.79 (1H, ddd, J8, 7 and 2, 5'-H), 7.59 (1H, ddd, J8.5, 7 and 2, 6'-H) and 8.38 (2 H, s, 4- and 6-H); m/z 336 (M$^+$), 335, 237, 223, 208, 195 and 155.

(+)-2-(2',3'-Difluoro-4'-octyloxyphenyl)-5-[(2S,3S)-2-chloro-3-methylpentanoyloxy]pyrimidine 37.—Trimethylamine (234 mg, 2.31 mmol) was added to a solution of the difluorophenylhydroxy-pyrimidine 35 (740 mg, 2.31 mmol) and (2S, 3S)-2-chloro-3-methylpentanoyl chloride 36 (388 mg, 2.31 mmol) in dry dichloromethane (8 ml) with stirring under nitrogen at room temperature for 2 h. Dichloromethane was added and the mixture was washed with dilute hydrochloric acid (twice), saturated sodium bicarbonate solution and brine, dried and evaporated. The residue was purified by flash chromatography (10% ethyl acetate-light petroleum) to give the ester 37 (670 mg, 58%) (from MeOH), m.p 66.2° C., $[\alpha]_D^{26}$+1.5° (c 2.4 in CHCl$_3$); $v_{max}$/cm$^{-1}$(KBr) 2920, 1765 (CO), 1615, 1510, 1470, 1420, 1300, 1230, 1120 and 1080; δ 0.89 (3H, t,J6.5, Me), 1.00 (3H, t,J6.5, CH$_3$CH$_2$CH(CH$_3$), 1.15 (3H, d,J7, CH(CH$_3$)), 1.25–1.55 (10H, m), 1.76 (2H, m, CH$_3$CH$_2$CH(CH$_3$), 1.85 (2H, quint, OCH$_2$CH$_2$), 2.25 (1H, m, CHMe), 4.11 (2H, d, J6.5, OCH$_2$), 4.44 (1H, d, J7, CHCl), 6.84 (1H, ddd, J8, 7 and 2, 5'-H), 7.85 (1H, ddd, J8, 7 and 2, 6'-H) and 8.71 (2H, s 4- and 6-H); m/z 470 (M$^+$), 468 (M$^+$), 358 (M$^+$–C$_8$H$_{16}$), 356 (M$^+$–C$_8$H$_{16}$), 336, 237 and 224.

2-(2',3'-Difluoro-4'-octyloxyphenyl)-5-non-1-ynylpyrimidine 38.—Non-1-yne (1.0 ml, 6.4 mmol) was added via syringe to degassed mixture of 2-(2',3'-difluoro-4'-octyloxyphenyl)-5-bromopyrimidine 4 (1.27 g, 3.18 mmol), tetrakis(triphenylphosphine)palladium (173 mg, 0.15 mmol) and copper(I) iodide (29 mg, 0.15 mmol) in diisopropylamine (60 ml) under nitrogen. The mixture was heated under gentle reflux for 4 h. The solvent was removed in vacuo and the residue was purified by flash chromatography (5% ethyl acetate-light petroleum, the sample was preloaded onto silica in dichoromethane) to give the nonynylpyrimidine 38 (1.29 g, 92%) (from MeOH), transitions/° C. K 64.4 (N 63.3) I; $v_{max}$/cm$^{-1}$(KBr) 2920, 2850, 2220, 1615, 1520, 1470, 1430s, 1295, 1205 and 1090s, δ 0.90 (6H, m), 1.20–1.55 (18H, m), 1.64 (2H, quint, J7, CH$_2$CH$_2$C≡C), 1.85 (2H, quint, J7, OCH$_2$CH$_2$), 2.46 (2H, t, J7, CH$_2$C≡C), 4.10(2H, t, J7, OCH$_2$), 6.83 (1H, ddd, J8, 7 and 2, 5'-H), 7.85 (1H, ddd, J8, 7 and 2, 6'-H) and 8.79 (2H, s, 4-and 6-H); m/z 442 (M$^+$), 330, 288, 287, 274, 273, 247 and 220.

2-(2',3'-Difluoro-4'-octyloxyphenyl)-5-nonylpyrimidine 39.—The nonynylpyrimidine 38 (1.50 g, 3.39 mmol) was hydrogenated over 5% Pd/C in ethyl acetate to give the nonylpyrimidine 39 (1.39 g, 92%) (from MeOH/EtOH), transitions/° C. K 42.8 S$_C$ 53.6 I; $v_{max}$/cm$^{-1}$(KBr) 2920, 2950, 1625, 1540, 1475, 1465, 1430, 1310, 1200 and 1080s; δ 0.90(6H, m, Me×2), 1.16–1.56 (22H, m), 1.67 (2H, quint, ArCH$_2$CH$_2$), 1.85 (2H, quint, OCH$_2$CH$_2$), 2.63 (2H, t, ArCH$_2$), 4.10 (2H, t, OCH$_2$), 6.82 (1H, ddd, J8.5, 8 and 2, 5'-H), 7.80 (1H, ddd, J8.5, 8 and 2, 6'-H) and 8.65 (2H, s, 4- and 6-H); m/z 446 (M$^+$), 334, 305, 277, 263, 249, 235 and 222.

2-(4-Trifluoromethylphenyl)-5-pent-1-ynylpyrimidine 40.—Quantities: 2-[4'-Trifluoromethylphenyl]-5-bromopyrimidine 10 (1.48 g, 4.88 mmol), pent-1-yne (0.96 ml, 9.76 mmol), tetrakis(triphenylphosphine)palladium (350 mg, 0.30 mmol), copper(I) iodide (57 mg, 0.30 mmol), diisopropylamine (20 ml). The experimental procedure was as described for compound 38 to give the pentynylpyrimidine 40 (1.22 g, 86%) (from MeOH), m.p. 140.5° C., $v_{max}$/cm$^{-1}$(KBr) 2970, 2200(C≡C), 1520, 1430, 1325s, 1165, 1115, 1075 and 1015, ≡ 1.07(3H, t, Me), 1.68 (2H, sext, CH$_2$CH$_3$), 2.47 (2H, t, CH$_2$C≡C), 7.74 (2H, d, 3'- and 5'-H), 8.55(2H, d, 2' and 6'-H) and 8.79 (2H, s, 4- and 6-H); m/z 290 (M$^+$), 275, 261, 248, 172 and 152.

2-(4-Trifluoromethylphenyl)-5-pentylpyrimidine 41.—The pentynylphenylpyrimidine 40 (1.00 g, 3.45 mmol) was hydrogenated over 5% Pd/C in ethyl acetate to give the arylpentylpyrimidine 41 (0.96 g, 95%) (from MeOH/H$_2$O), transitions/° C. K 51.0 (S$_A$ 42.1) 1; $v_{max}$/cm$^{-1}$(KBr) 2930, 2860, 1545, 1430, 1315s, 1165, 1140, 1070 and 1015, δ 0.91 (3H, t, Me), 1.37 (4H, m), 1.69 (2H, quint, ArCH$_2$CH$_2$), 2.66 (2H, t, ArCH$_2$), 7.75 (2H, d, 3'- and 5'-H), 8.54(2H, d, 2'- and 6'-H) and 8.66 (2H, s, 4- and 6-H); m/z 294 (M$^+$), 275, 251, 237 (M$^+$–C$_4$H$_9$), 224, 210 and 172.

2-(4'-Fluorophenyl)-5-pent-1-ynylpyrimidine 42.—Quantities: 2-(4'-fluorophenyl)-5-bromo-pyrimidine 20 (1.48 g, 4.88 mmol), pent-1-yne (0.98 ml, 10 mmol), tetrakis (triphenylphosphine)palladium (350 mg, 0.30 mmol), copper(I) iodide (57 mg, 0.30 mmol), diisopropylamine (20 ml). The experimental procedure was as described for compound 38. The crude product was purified by flash chromatography (8% ethyl acetate-light petroleum) to give the fluorophenylpyrimidine 42 (1.02 g, 85%), m.p. 51° C.; $v_{max}$/cm$^{-1}$(KBr) 2960, 2870, 2220, 1600, 1510, 1430, 1220, 1150 and 855; δ 1.07 (3H, t, Me), 1.68 (2H, sext, CH$_2$CH$_3$), 2.47 (2H, t, CH$_2$C≡C), 7.18 (2H, t, 3'- and 5'-H), 8.44 (2H, dd, 2'- and 6'-H) and 8.75 (2H, s, 4- and 6-H); m/z 240 (M$^+$), 225, 212, 198, 184, 171 and 118.

2-(4'-Fluorophenyl-5-pentylpyrimidine 43.—The pentynylpyrimidine 42 (0.91 g, 3.79 mmol) was hydrogenated over 5% Pd/C in ethyl acetate to give the pentylpyrimidine 43 (0.81 g, 87%) (from MeOH), m.p. 28.6° C.; $v_{max}$/cm$^{-1}$(KBr) 2920, 2850, 1595, 1580, 1540, 1430, 1220, 1150, 1090, 930 and 850; δ 0.91 (3H, t, Me), 1.29–1.42 (4H, m), 1.65 (2H, quint, ArCH$_2$CH$_2$), 2.61 (2H, t, ArCH$_2$), 7.15 (2H, t, 3'- and 5'-H), 8.42 (2H, dd, J 9 and 6, 3'- and 5'-H) and 8.60 (2H, s, 4- and 6-H); m/z 244 (M$^+$), 201, 187, 174 and 160.

2-(3',4'-Difluorophenyl)-5-pent-1-ynylpyrimidine 44.—

2-(3',4'-Difluorophenyl)-5-pentylpyrimidine 45.—The difluorophenylpentynylpyrimidine 44 (322 mg, 1.25 mmol) was hydrogenated over 5% Pd/C in ethyl acetate to give the difluorophenylpentylpyrimidine 45 (304 mg, 93%), b.p. 220° C. at 1 mmHg (Kugelrohr distillation);$v_{max}$/cm$^{-1}$(KBr) 2930, 2860, 1585, 1540, 1515, 1435s, 1330, 1265, and 1190; δ 0.92 (3H, t, Me), 1.20–1.44 (4H, m), 1.66 (2H, quint, ArCH$_2$CH$_2$), 2.63 (2H, t, ArCH$_2$), 7.24 (1H, m, 5'-H), 8.16–8.33 (2H, m, 2'- and 6'-H) and 8.61 (2H, s, 4- and 6-H); m/z 262 (M$^+$), 244, 219, 205, 187, 178 and 139.

2-[2',3'-Difluoro-4'-(trans-4"-pentylcyclohexylethylphenyl]pyrimidine-5-carboxylic acid 46.—To a degassed solution of the bromopyrimidine 16 (1.89 g, 4.19 mmol) in THF (100 ml) cooled to –100° C. was added dropwise with stirring 2.5M butyllithium (1.8 ml, 4.4 mmol) at such a rate to maintain the temperature below –90° C. and stirred at ca. –95° C. for 0.5 h. The orange mixture was poured onto a rapidly stirring suspension of powdered CO$_2$ in dry ether and, after reaching ambient temperature, was acidified with dilute sulphuric acid. The crude product was extracted into ether (twice), washed with brine, dried (MgSO$_4$) and evaporated. Flash chromatography (5% methanol-dichloromethane) gave the carboxylic acid 46 (1.13 g, 65%) (from EtOH/THF), m.p. 190° C., $v_{max}$/cm$^{-1}$ (KBr) 3200-2400br, 1675 (CO), 1580, 1460, 1405, 1290 and 900; δ 0.90 (7H, m), 1.07–1.38 (10H, m), 1.56 (2H, q), 1.80 (4H, t), 2.74 (2H, ArCH$_2$), 7.09 (1H, t, 5'-H), 7.36 (1H, t, 6'-H) and 9.37 (2H, s, 4- and 6-H).

(R)-(-)-2-Fluorooctyl 2-[2',3'-Difluoro-4'-(trans-4"-pentylcyclohexylethyl)phenyl]-pyrimidine-5-carboxylate 47.—DEAD (266 mg, 1.53 mmol) was added dropwise with stirring to a solution of (R)-(+)-2-fluorooctanol (227 mg, 1.53 mmol), triphenylphosphine (402 mg, 1.53 mmol) and the acid 46 (639 mg, 1.53 mmol) in THF (15 ml) at ambient temperature. After 24 h the solvent was removed in vacuo and the residue was purified by flash chromatography (5 to 10% ethyl acetate-light petroleum, the sample was adsorbed onto silica in dichloromethane) to give the ester 47 (613 mg, 76%) (from EtOH), transitions/° C. K 91.5 N* 109.1 BP 109.7 I, $[\alpha]_D^{25}$ −3.3° (c 1.1 in CHCl$_3$); $v_{max}$/cm$^{-1}$(KBr) 2920. 2850, 1720(CO), 1590, 1465, 1430, 1290, 900 and 805; δ 0.88 (10H, m), 1.12–1.40(16H, m), 1.55 (4H, m), 1.79(6H, m), 2.74(2H, t, J 8, ArCH$_2$), 4.46(1H, ddd, $^3J_{HF}$ 21, J$_{gem}$. 13 and J 6.5, OCH$_2$), 4.54 (1H, ddd, $^3J_{HF}$ 27, J$_{gem}$. 13 and J 2.5, OCH$_2$), 4.82 (1H, br, d, $^2J_{HF}$ 49, CHF), 7.07 (1H, ddd, J 7.5, 7 and 2, 5'-H), 7.87 (1H, ddd, J 7.5, 7 and 2, 6'-H) and 9.39 (1H, s, 4'- and 6'-H); m/z 393, 380 (M$^+$−OCH$_2$CHFC$_6$H$_{13}$), 250, 204 and 152.

2-[2',3'-Difluoro-4'-(trans-4"-pentylcyclohexylethyl) phenyl]-5-hydroxypyrimidine 48.—Quantities bromopyrimidine 16 (3.72 g, 8.25 mmol), 1.6M butyllithium (5.7 ml, 9.1 mmol), trimethyl borate (1.9 ml, 16.5 mmol), THF (80 ml), 30% hydrogen peroxide (3.7 ml, 33 mmol). The experimental procedure was as described for compound 33. The crude product was purified by flash chromatography (10 to 30% ethyl acetate-light petroleum) to give the hydroxypyrimidine 48 (1.82 g, 57%) (from MeOH), m.p. 157.3° C.; $v_{max}$/cm$^{-1}$(KBr) 2920, 2720, 2580, 1505, 1430, 1280, 1240 and 1180 δ 0.85 (7H, m), 1.05–1.38 (10H, m), 1.50 (2H, m), 1.73 (4H, t), 2.68 (2 H, t, ArCH$_2$), 7.01 (1H, ddd, 5'-H), 7.55 (1H, ddd, 6'-H), 8.37 (2H, s, 4- and 6-H) and 9.7 (1H, br s); m/z 388 (M$^+$), 317 (M$^+$−C$_5$H$_{11}$), 235, 222 and 204.

(R)-(-)-2-[2',3'-Difluoro-4'-(trans-4"-pentylcyclohexylethyl)phenyl]-5-(2-fluorooctyloxy)-pyrimidine 49.—Quantities: DEAD (448 mg, 2.58 mmol) in THF (3 ml), (R)-(+)-2-fluorooctanol (379 mg, 2.58 mmol), hydroxypyrimidine 48 (1.0 g, 2.58 mmol), triphenylphosphine (676 mg, 2.58 mmol). The experimental procedure was as described for compound 34. The crude product was purified by flash chromatography (5 to 7% ethyl acetate-light petroleum) to give the 2-fluorooctyloxypyrimidine 49 (820 mg, 61%) (from EtOH), transitions/° C. K 102.2 N* 128.3 I; $[\alpha]_D^{26}$ −2.4° (c 2.0 in CHCl$_3$); $v_{max}$/cm$^{-1}$(KBr) 2920, 2845, 1540, 1460, 1435s, 1285 1085, and 900; δ 0.80–1.03 (10H, m), 1.06–1.45 (16H, m), 1.55 (4H, m), 1.82 (6H, m), 2.71 (2H, t J 8, ArCH$_2$), 4.22 (2H, dd, $^3J_{HF}$ 22 and J 4, OCH$_2$), 4.86 (1H, d of sext, $^2J_{HF}$ 48 and J 4, CHF), 7.01 (1H, ddd, J 7.5, 7 and 1.5, 5'-H), 7.67 (1H, ddd, J 7.5, 7 and 1.5, 5'-H) and 8.53 (2H, s, 4- and 6-H); m/z 518 (M$^+$), 489, 475, 461, 447, 365 and 353.

(S)-2-[2',3'-Difluoro-4'-(trans-4'-pentylcyclohexylethylphenyl]-5-(2-methylheptyloxy) pyrimidine 50.—Quantities: hydroxypyrimidine 48 (200 mg, 0.51 mmol), triphenylphosphine (135 mg, 0.51 mmol), DEAD (90 mg, 0.51 mmol), (R)-(−)-octan-2-ol (67 mg, 0.51 mmol), THF (8 ml). The experimental procedure was as described for compound 34. The crude product was purified by flash chromatography (3 to 5% ethyl acetate-light petroleum) to give the ether 50 (170 mg, 66%) (from EtOH), transitions/° C. K 44.7 (N* 44.5) I; $[\alpha]_D^{24}$ 0.0° (c 1.8 in CHCl$_3$); $v_{max}$/cm$^{-1}$(KBr) 2920, 2850, 1570, 1530, 1460, 1430s, 1270, 1050 and 900, δ 0.81–1.04 (10H, m), 1.11–1.65 (23H, m), 1.79 (6H, m), 2.71 (2H, t, J 8, ArCH$_2$), 4.49 (1H, sext, J 6, OCHMe), 7.02(1H,ddd,J7.5, 7and 1.5, 5'-H), 7.67(1H, ddd,J7.5, 7and 1.5, 5'-H) and 8.49(2H, s ,4- and 6-H); m/z 500 (M$^+$), 388 (M$^+$−C$_8$H$_{16}$), 360, 317, 235, 222 and 204.

2-[2',3'-Difluoro-(trans-5"-hexyl-1",3"-dioxan-2"-yl) phenyl]pyrimidine-5-carboxylic acid 51.—Quantities: dioxanylphenylpyrimidine 18 (1.5 g, 3.4 mmol), 2.5M butyllithium (1.4 ml, 3.6 mmol), THF (60 ml). The experimental procedure was as described for compound 46. Saturated ammonium chloride solution was added to the lithium carboxylate. The mixture was extracted with ethyl acetate (twice) and the organic solution was washed with brine, dried (Na$_2$SO$_4$) and evaporated to give the acid 51 (1.19 g, 86%) (from MeOH), m.p.>300° C., $v_{max}$/cm$^{-1}$(KBr) 2920, 2670br, 2560br, 1690 (CO), 1590, 1460, 1410, 1305, 1095 and 805; δ 0.90 (3H, t, Me), 1.05–1.20(2H, m), 1.20–1.45 (8H, m), 2.14(1H, m, CH(CH$_2$O)$_2$),3.59(2H, t,J 11, 4"$_{ax}$.- and 6"$_{ax}$.-H), 4.23 (2H, dd, J 11 and 4, 4"$_{eq}$- and 6"$_{eq}$-H), 5.35 (1H, br, s), 5.75 (1H, s, ArCH), 7.51 (1H, ddd, 5'-H), 7.97 (1H, ddd, 6'-H) and 9.36 (2H, s, 4- and 6-H); m/z 406 (M$^+$), 282, 266, 236, 232, 219 and 166.

(R)-(-)-2-Fluorooctyl-2-[2',3'-Difluoro-4'-(trans-5"-hexyl-1",3"-dioxan-2"-yl)phenyl]pyrimidine-5-carboxylate 52.—Quantities: dioxanylphenylpyrimidinecarboxylic acid 51 (617 mg, 1.52 mmol), DEAD (264 mg, 1.57 mmol), triphenylphosphine (398 mg, 1.52 mmol), (R)-(+)-2-fluorooctanol (225 mg, 1.52 mmol), THF (10 ml). The experimental procedure was as described for compound 47. Flash chromatography (10% ethyl acetate-light petroleum) of the reaction mixture gave the ester 52 (660 mg, 83%) (from hexane), m.p. 136° C., $[\alpha]_D^{27}$ −5.5° (c 1.3 in CHCl$_3$), $v_{max}$/cm$^{-1}$(KBr) 2920, 2850, 1735sh (CO), 1720 (CO), 1585, 1460, 1285, 1130, 1035 and 950; δ 0.90 (6H, m), 1.14 (2H, m), 1.22–1.63 (19H, m), 1.78 (1H, m), 2.19 (1H, m, CH(CH$_2$O)$_2$), 3.58 (2H, t, J 11, 4"$_{ax}$.- and 6"$_{ax}$.-H), 4.25 (2H, dd, J 11 and 4, 4"$_{eq}$.- and 6"$_{eg}$.-H) 4.46 (1H, ddd $^3J_{HF}$ 21, J$_{gem}$. 13 and J 6.5, OCH$_2$), 4.55 (1H, ddd, $^3J_{HF}$ 27, J$_{gem}$. 13 and J 2.5, OCH$_2$), 4.82 (1H, br d, $^2J_{HF}$ 49, CHF), 5.76 (1H, s, ArCH), 7.52 (1H, ddd, J 8, 6 and 2, 5'-H), 7.99 (1H, ddd, J 8, 6 and 2, 6'-H) and 9.40 (2H, s, 4- and 6-H), m/z 536 (M$^+$), 535, 506, 477, 411, 395, 367, 351 and 247

2-[2',3'-Difluoro-4'-(cis/trans-4"-propylcyclohexyl) phenyl]pyrimidine-5-carboxylic acid 53.—Quantities: cis/trans-bromopyrimidine 22 (2.27 g, 5.62 mmol), 2.5M butyllithium (2.5 ml, 6.2 mmol), THF (150 ml), hexane (15 ml). The experimental procedure was as described for compound 46 to give the acid 53 as a mixture of isomers (1.87 g, 90%) (from EtOH/toluene); $v_{max}$/cm$^{-1}$(KBr) 2925, 2860, 2660br, 2550br, 1690 (CO), 1585, 1460, 1405, 1300 and 905; δ [CDCl$_3$/(CD$_3$)$_2$SO] 0.91 and 0.94 (3H, overlapping t, cis/trans-Me), 1.01–1.58 (m), 1.59–1.82 (m), 1.90 (d, J 10, trans-cyclohexyl eq.-H), 2.93 (1H, m, ArCH), 7.14 and 7.17 (1H, overlapping ddd, J 7.5, 7 and 2, cis/trans 5'-H), 7.89 (1H, ddd, J 8, 7 and 2, 6'-H) and 9.36 (2H, s, 4-and 6-H); m/z 360 (M$^+$), 341, 317, 311, 297, 276 and 262.

(R)-(-)-2-Fluorooctyl 2-[2',3'-Difluoro-4'-(cis/trans-4"-propylcyclohexyl)phenyl]pyrimidine-5-carboxylate 54.— Quantities: cis/trans-cyclohexylphenylpyrimidinecarboxylic acid 53 (671 mg, 1.86 mmol), DEAD (325 mg, 1.86 mmol), triphenylphosphine (488 mg, 1.86 mmol), (R)-(+)-2- fluorooctanol (276 mg, 1.86 mmol), THF (8 ml). The experimental procedure was as described for compound 47. Flash chromatography (5 to 10% ethyl acetate-light petroleum) of the reaction mixture gave the ester 54 as a mixture of isomers in a ratio (1.4:1) determined by HPLC (676 mg, 74%), $[\alpha]_D^{27}$ −5.4° (c 1.3 in CHCl$_3$); $\nu_{max}$/cm$^{-1}$ (KBr) 2920, 2860, 1720 (CO), 1590, 1450, 1430. 1290, 1140. 900 and 810; δ 0.80–0.98 (6H, m), 1.0–2.0 (23H, m), 2.94 (1H, m, ArCH), 4.46 (1H, ddd, $^3J_{HF}$ 21,$J_{gem.}$ 13 and J6.5, OCH$_2$), 4.55 (1H, ddd, $^3J_{KF}$27, $J_{gem.}$ 13 and J2.5, OCH$_2$), 4.81 (1H, br d, $^2H_{HF}$ 49, CHF), 7.12 and 7.15 (1H, m, 5'-H cis/trans isomers), 7.90 (1H, ddd, J 8, 6 and 2, 6'-H) and 9.39 (2H, s, 4- and 6-H); m/z 490 (M$^+$), 447(M$^+$−C$_3$H$_7$), 361, 343, 331, 275, 263 and 245.

1-(4'-Octyloxyphenyl)-2-[5"-(4-hexyloxyphenyl) pyrimidine-2"-yl]ethyne 56.—Quantities: bromopyrimidine 32 (1.05 g, 2.83 mmol), 4-hexyloxyphenylboronic acid 55 (0.87 g, 3.96 mmol), tetrakis(triphenylphosphine)palladium (162 mg, 0.14 mmol), DME (50 ml), 2M sodium carbonate (50 ml). The experimental procedure was as described for compound 4. The crude product was purified by flash chromatography (10 to 20% ethyl acetate-light petroleum) to give the tolane 56 (0.90 g, 66%) (from EtOH), transitions/° C. K 105.5 S$_C$172.3 N 217.0 I; $\nu_{max}$/cm$^{-1}$(KBr) 2920, 2850, 2220 (C≡C), 2200 (C≡C), 1595, 1505, 1420, 1285, 1250, 1180, 1160 and 825; δ 0.90 (6H, m), 1.20–1.67 (16H, m), 1.80 (4H, m, OCH$_2$CH$_2$), 4.00 (4H, m, OCH$_2$), 6.89 (2H, d), 7.04 (2H, d), 7.53 (2H, d), 7.62 (2H, d) and 8.90 (2H, s, 4- and 6-H); m/z 484 (M$^+$), 470, 456, 399, 372. 360. 341 and 262

1-(4'-Octyloxyphenyl)-2-[5"-nonynylpyrimidin-2"-yl] ethyne 57.—Quantities: bromopyrimidine 32 (1.35 g, 3.64 mmol), non-1-yne (0.90 g, 7.3 mmol), tetrakis (triphenylphosphine)palladium (189 mg, 0.16 mmol), copper(I) iodide (31 mg, 0.16 mmol), diisopropylamine (40 ml), dichloromethane (15 ml) (necessary for increased solubility). The experimental procedure was as described for compound 38. The crude product was purified by flash chromatography (8% ethyl acetate-light petroleum) to give the dialkynylpyrimidine 57 (0.71 g, 45%) (from hexane), transitions/° C. K 94.2 (N 89.8) I; $\nu_{max}$/cm$^{-1}$(KBr) 2920, 2850, 2120 (C≡C), 2200 (C≡C), 1600, 1560, 1505, 1420, 1290, 1245, 1165, 830 and 790; δ 0.88 (6H, m, Me), 1.24–1.51 (18H, m), 1.63 (2H, quint, J 7, ArCH$_2$CH$_2$), 1.79 (2H, quint, J 6.5, OCH$_2$CH$_2$), 2.46 (2H, t, J 7, ArCH$_2$), 3.98(2H, t,J6.5, OCH$_2$), 6.88(2H, d,J9, 3'-and 5'-H), 7.59 (2H, d,J9, 2'- and 6'-H) and 8.69 (2H, s, 4"- and 6"-H); m/z 430 (M$^+$), 345, 318 (M$^+$−C$_8$H$_{16}$), 289, 275, 261, 248, 235 and 208.

2-(4'-Benzyloxyphenyl)pyrimidine-5-carboxylic acid 58.—Quantities: benzyloxyphenylbromopyrimidine 26 (2.17 g, 6.36 mmol), 1.6M butyllithium (4.4 ml, 7.0 mmol), THF (80 ml). The experimental procedure was as described for compound 46. The crude product was triturated with hot light petroleum (b.p. 60–80° C.) and the undissolved solid yielded the pyrimidine carboxylic acid 58 (1.4 g, 72%) (from MeOH), m.p. 299° C.; $\nu_{max}$/cm$^{-1}$(KBr) 3050br, 1690, 1575, 1380, 1300, 1250, 1170, 1020 and 800; δ[CDCl$_3$, (CD$_3$)$_2$SO] 5.21 (2H, s, OCH$_2$), 7.17 (2H, d, 3'- and 5'-H), 7.4–7.54(5H, m, Ph), 8.43 (2H, d, 2'- and 6'-H) and 9.19 (2H, s, 4- and 6-H); m/z 306 (M$^+$), 215, 187, 141, 119 and 91.

2-(4'-Hydroxyphenyl)pyrimidine-5-carboxylic acid 59.The acid 58 (1.35 g, 4.11 mmol) was hydrogenolysed in ethyl acetate over 5% Pd/C to give the hydroxy acid 59 (0.74 g, 83%) (from EtOH), m.p. dec. $\nu_{max}$/cm$^{-1}$(KBr) 2660, 2560, 1680, 1575, 1400, 1385, 1290, 1250 and 1170; δ [(CD$_3$)$_2$SO] 6.91 (2H, d, 3'- and 5'-H), 8.31 (2H, d, 2'- and 6'-H) and 9.16(2H, s, 4- and 6-H); m/z 216 (M$^+$), 181, 171, 144 and 119.

(S)-(+)-1-Methylheptyl 2-(4'-Hydroxyphenyl)-pyrimidine-5-carboxylate 60.—Quantities: hydroxy acid 59 (716 mg, 3.28 mmol), DEAD (572 mg, 3.28 mmol), triphenylphosphine (861 mg, 3.28 mmol), (R)-(−)-octan-2-ol (428 mg, 3.28 mmol), THF (100 ml). The experimental procedure was as described for compound 47. Flash chromatography (10% ethyl acetate-light petroleum) gave the 1-methylheptyl ester 60 (520 mg, 48%) (from EtOH/AcOH), m.p.98.8° C., $[\alpha]_D^{22}$ +44.7° (c 1.7 in CHCl$_3$); $\nu_{max}$/cm$^{-1}$ (KBr) 3440br, 2920, 1670, 1570, 1430, 1345, 1300, 1165 and 810; δ 0.88 (3H, t), 1.20–1.50 (11H, m), 1.70 (2H, m, CH$_2$CHMe), 5.22 (1H, sext, OCHMe), 6.10 (1H, br s), 6.94 (2H, d, 3'- and 5'-H), 8.42 (2H, d, 2'- and 6'-H) and 9.27 (2H s, 4- and 6-H); m/z 328 (M$^+$),314, 285, 261, 247 216 and 119.

(S)-(+)-1-Methylheptyl 2-[4'-(4-tetradecyloxybenzoyloxy)phenyl]pyrimidine-5-carboxylate 61.—The hydroxy ester 60 (410 mg, 1.25 mol), 4-tetradecyloxybenzoic acid (417 mg, 1.25 mmol), DCC (257 mg, 1.25 mmol) and dimethylaminopyridine (cat.) in dry dichloromethane (15 ml) were stirred for 48 h at room temperature. Flash silica was added and the solvent was removed in vacuo and the residue was purified by flash chromatography (10% ethyl acetate-light petroleum) to give the ester 61 (230 mg, 28%) (from EtOH/MeOH), transitions/° C. I TGB(fog) TGB(C or A) S$_C$ 88 S$_{Cferri1}$ 81.4 S$_{Cferri2}$ S$_{Canti}$ 69 K (m.p. 85.4° C.); $[\alpha]_D^{19}$ +20.2° (c 1.9 in CHCl$_3$); $\nu_{max}$/cm$^{-1}$(KBr) 2880, 1705 (CO), 1690 (CO), 1610, 1460, 1290, 1240, 1195, 1110 and 830; δ 0.88 (6H, m), 1.20–1.60 (33H, m), 1.60–1.90 (4H, m), 4.05 (2H, t, J 6, OCH$_2$), 5.22 (1H, sext, J 6, OCHMe), 6.98 (2H, J 8, 3'- and 5'-H), 7.37 (2H, d, J 8, ArH), 8.16 (2H, d, J 8, ArH), 8.60(2H, d, J8, 2'- and 6'-H) and 9.31 (2H,s,); m/z 642 (M$^+$−2), 419,317,265 and 121.

1(4'-Octyloxyphenyl)-2-[5"-(2,3-difluoro-4-pentylphenyl)pyrimidin-2"-yl]ethyne 62.—Quantities: bromopyrimidine 32 (1.48 g, 3.82 mmol), difluorophenylboronic acid 23 (1.74 g, 7.64 mmol), tetrakis (triphenylphosphine)palladium (88 mg, 0.076 mmol), DME (140 ml), dichloromethane (5 ml), 2M sodium carbonate (75 ml). The experimental procedure was as described for compound 4. The crude product was purified by flash chromatography (10% ethyl acetate-light petroleum) to give the pyrimidine 62 (0.74 g, 40%) (from EtOH), transitions/° C. K 105.5 S$_C$ 112.6N 168.7 I; $\nu_{max}$/cm$^{-1}$(KBr) 2920, 2850, 2220 (C≡C), 2200 (C≡C), 1600, 1510, 1460, 1425, 1290, 1250, 1165 and 890; δ 0.89 (3H, t, Me), 0.92 (3H, t, Me), 1.26–1.50 (14H, m), 1.66 (2H, quint, ArCH$_2$CH$_2$), 1.80 (2H, quint, OCH$_2$CH$_2$), 2.72 (2H, t, J 7.5, ArCH$_2$), 3.90 (2H, t,J 6.5, OCH$_2$), 6.90 (2H, d, J 9, 3'- and 5'-H), 7.09 (1H, ddd, J 8, 6.5 and 2, 6-H), 7.15 (1H, ddd, J 8, 6.5 and 2, 5-H), 7.63 (2H, d, J 9, 2'- and 6'-H) and 8.91 (2H, d, J 1.5, 4"- and 6"-H); m/z 490 (M$^+$), 379, 350, 335, 322, 206 and 151.

2-[2',3'-Difluoro-4'-(cis/trans-4"-propylcyclohexyl) phenyl]-5-(4"-octyloxyphenyl)pyrimidine 63.—Quantities: cis/trans-bromopyrimidine 22 (1.09 g, 2.75 mmol), 4-octyloxyphenylboronic acid 7 (1.03 g, 4.13 mmol), tetrakis(triphenylphosphine)palladium (159 mg, 0.18 mmol), DME (50 ml), dichloromethane (5 ml), 2M sodium carbonate (50 ml). The experimental procedure was as described for compound 4. The crude product was purified by flash chromatography (10% ethyl acetate-light petroleum) to give the pyrimidine 63 as a mixture of isomers in a ratio (1.5:1) determined by HPLC (1.17 g, 82%) (from EtOH/EtOAc); $\nu_{max}$/cm$^{-1}$(KBr) 2920, 2850, 1605, 1530, 1510, 1450, 1430, 1245, 1180, 900 and 830; δ 0.85–0.97 (6H, m), 1.23–1.97 (25H, m), 2.93(1H, m ArCH), 4.02(2H, t,J7, OCH$_2$), 7.05 (2H, d,J8, 3'''- and 5'''-H), 7.14 (1H, ddd, J 8, 6.5 and 2, 5'-H), 7.57 (2H, d, J 8, 2'''- and 6'''-H), 7.82 (1H, ddd, J 8, 6.5 and 2, 5'-H) and 9.02 (2H, s, 4- and 6-H); m/z 520 (M$^+$), 408 (M$^+$–C$_8$H$_{16}$), 389, 379, 365, 323, 310, 297 and 118.

Ethyl 2-fluorooctanoate 65.—A mixture of acetamide (49 g) and ethyl 2-bromooctanoate 64 (100 ml, 0.464 mol) was heated at 80° C. (reaction temperature) with mechanical stirring under nitrogen until homogeneous. Anhydrous potassium fluoride (49.3 g, 0.84 mol) was added followed by tetrabutylammonium fluoride (3.25 ml). The mixture was heated for 5 h at 140° C. with rapid stirring and allowed to cool to 90° C. prior to pouring into ice (400 ml). The reaction vessel was rinsed with water and dichloromethane which were added to the ice mixture. The aqueous phase was extracted with dichloromethane (3 times); the combined organic solutions were dried (Na$_2$SO$_4$) and filtered. The solution was cooled to 5° C. under nitrogen and bromine (19.3 ml, 0.375 mol) was added. After 3 h saturated sodium thiosulfate solution (150 ml) was added. The organic phase was washed with sat. sodium bicarbonate solution (twice) and brine, dried (Na$_2$SO$_4$) and evaporated. The residue was distilled to give pure ethyl 2-fluorooctanoate 65 (33.9 g, 38%); b.p. 56–61° C. at 0.5 mm Hg; $v_{max}$/cm$^{-1}$(film) 2930, 2860, 1760, 1740, 1370, 1275, 1205, 1090 and 1030; δ 0.88 (3H, t, Me), 1.20–1.56 (11H, m), 1.75–2.13 (2H, m), 4.26 (2H, q, ) and 4.90(1H, $^2$J$_{HF}$46 and J8, CHF); m/z 190 (M$^+$), 185, 168, 161, 143, 129, 113 and 106.

Partial Resolution of of Ethyl 2-fluorooctanoate by Enzyme Catalysed Hydrolysis.-Ethyl 2-fluorooctanoate 65 (71.6 g, 0.377 mol) was added to 0.063M phosphate buffer (pH 7.0) (280 ml) and deionised water (280 ml) in a beaker fitted with a pH electrode, magnetic stirrer bar and a cooling bath. Pseudomonas lipase (Amano PS) (22 mg) was added and the mixture was stirred at ca 5° C. The pH was maintained at ca. 7 by adding 1.0M sodium hydroxide solution via a syringe pump. Hydrolysis continued until 151 ml of the hydroxide solution had been added (40% conversion). The mixture was extracted with ether (3 times) and the combined organic solutions were washed with brine, dried (K$_2$CO$_3$) and evaporated to give partially resolved (R)-ester. The aqueous layer was acidified to pH 2.7 with conc. hydrochloric acid and extracted with ether. The organic solutions were dried and evaporated to give partially resolved (S)-(-)-2-fluorooctanoic acid. Concentrated sulphuric acid (2 ml) was added to (S)-2-fluorooctanoic acid (24.0 g, 0.15 mol) in ethanol (200 ml) and the solution was heated under reflux for 4 h. Most of the ethanol was distilled off at atmospheric pressure; dichloromethane was added and the solution was washed with sat. sodium bicarbonate solution until neutral. brine, dried (MgSO$_4$) and evaporated. The yellow liquid was distilled to give partially resolved ethyl (S)-(-)-2-fluorooctanoate 66 (25.13g, 87%) b.p. 68° C. at 0.45 mm Hg.

Optical Purity enhancement of (S)-(-)-2-Fluorooctanoic acid.—Quantities: partially resolved ethyl (S)-(-)-2-fluorooctanoate 66 (25.1 g, 0.132 mol), 0.063M phosphate buffer (pH 7.0) (280 ml), deionised water (230 ml), Pseudomonas lipase (Amano PS) (30 mg), 1.0M sodium hydroxide solution (99 ml, 0.099 mol). The experimental procedure was the same as described for compound 66. The hydrolysis was continued until the total volume of sodium hydroxide solution was consumed (75% conversion) and the mixture was extracted with ether (3 times). The combined organic solutions were washed with brine, dried (K$_2$CO$_3$) and evaporated. The recovered ester was combined with the unreacted ester from the first hydrolysis (40% conversion) and used for the preparation of the (R)-(+)-ester. The aqueous layer was acidified to pH 2.7 with conc. hydrochloric acid and extracted with ether. The organic solutions were dried and evaporated. The liquid was distilled (Kugelrohr) to give (S)-(-)-2-fluorooctanoic acid 67 (16.0 g, 0.099 mol), b.p. 140° C. at 0.5 mm Hg; [α]$_D^{21}$=-8.3° (c 4.9 in CHCl$_3$); $v_{max}$/cm$^{-1}$(film) 3600-2400br, 2650sh, 2570sh, 1720br (CO), 1460, 1245, 1120, 1085 and 860; δ 0.88 (3H, t, Me), 1.20–1.43 (8H, m), 1.83–2.40 (2H, m, CH$_2$CHF), 4.97 (1H, ddd, J49, 7 and 5, CHF) and 10.50 (1H, br s, CO$_2$H).

Ethyl (R)-(+)-2-fluorooctanoate 69.—Quantities: partially resolved ethyl 2-fluorooctanoate 68 (44 g, 0.23 mol), 0.063M phosphate buffer (pH 7.0) (400 ml), deionised water (400 ml), Pseudomonas lipase (Amano PS) (40 mg). The experimental procedure was as described for compound 66. The hydrolysis was continued until the rate of reaction was almost zero, as indicated by a constant pH with zero addition of alkali (reaction time 5 h, 38 ml of 1M sodium hydroxide solution added i.e. 16% hydrolysis). The mixture was extracted with ether (3 times) and the combined organic solutions were washed with brine, dried (K$_2$CO$_3$) and evaporated. The liquid was distilled to give ethyl (R)-(+)-2-fluoroacetate 69 (30.7 g, 0.23 mol), b.p. 63° C. at 0.6 mm Hg; [α]$_D^{26}$=+8.5° (c 5.9 in CHCl$_3$).

(R)-(+)-2-Fluorooctanol 70.—Ethyl (R)-(+)-2-fluorooctanoate 69 (20.0 g, 105 mol) in dry THF (30 ml) was added dropwise with stirring to a suspension of lithium aluminium hydride (6 g, 0.158 mol) under nitrogen and with water bath cooling. After the final addition the water bath was removed and the mixture was stirred for 16 h. Aqueous THF (50 ml, 1:3) was added dropwise with iced water-bath cooling followed by 20% hydrochloric acid until a clear solution was effected. The mixture was extracted with ether (3 times) and the combined organic solutions were washed with sat. sodium bicarbonate solution (twice) and brine, dried (MgSO$_4$) and evaporated. The yellow oil was distilled to give (R)-(+)-2-fluorooctanol 70 which solidified on cooling (12.9 g, 83%), b.p. 110° C. at 20 mm Hg, [α]$_D^{18}$=+6.2° (c 4.6 in CHCl$_3$); $v_{max}$/cm$^{-1}$(film) 3600-3100br (OH), 2920, 2860, 1460, 1375, 1125sh, 1055br and 840; δ 0.90 (3H, t, Me), 1.14–1.80 (10H, m), 2.19 (1H, br s, OH), 3.69 (2H, br d, $^3$J$_{HF}$ 27, CH$_2$OH), and 4.56 (1H, br d, $^2$J$_{HF}$ 51, CHF); m/z 149 (M$^+$ 1), 137, 125, 115, 111, 97, 81 and 69.

Compounds of Formula III can be included in a material, the material being a mixture of compounds.

The materials of this aspect of the invention may be used in many of the known forms of liquid crystal display devices, for example chiral smectic electrooptic devices. Such a device may comprise a layer of liquid crystal material contained between two spaced cell walls bearing electrode structures and surface treated to align liquid crystal material molecules. The liquid crystal mixtures may have many applications including in ferroelectric, thermochromic and electroclinic devices.

Ferroelectric smectic liquid crystal materials, which can be produced by mixing an achiral host and a chiral dopant, use the ferroelectric properties of the tilted chiral smectic C, F, G, H, I, J and K phases. The chiral smectic C phase is denoted S$_c$* with the asterisk denoting chirality. The S$_c$* phase is generally considered to be the most useful as it is the least viscous. Ferroelectric smectic liquid crystal materials should ideally possess the following characteristics: low viscosity, controllable spontaneous polarisation (Ps) and an S$_c$ phase that persists over a broad temperature range, which should include ambient temperature and exhibits chemical and photochemical stability. Materials which possess these characteristics offer the prospect of very fast switching liquid crystal containing devices. Some applications of ferroelectric liquid crystals are described by J. S. Patel and J. W. Goodby in Opt. Eng., 1987, 26, 273.

In ferroelectric liquid crystal devices the molecules switch between different alignment directions depending on the polarity of an applied electric field. These devices can be arranged to exhibit bistability where the molecules tend to remain in one of two states until switched to the other switched state. Such devices are termed surface stabilised ferroelectric devices, eg as described in U.S. Pat. No. 5,061,047 and U.S. Pat. No. 4,367,924 and U.S. Pat. No. 4,563,059. This bistability allows the multiplex addressing of quite large and complex devices.

One common multiplex display has display elements, ie pixels, arranged in an x, y matrix format for the display of eg, alpha numeric characters. The matrix format is provided by forming the electrodes on one slide as a series of column electrodes, and the electrodes on the other slide as a series of row electrodes. The intersections between each column and row form addressable elements or pixels. Other matrix layouts are known, eg seven bar numeric displays.

There are many different multiplex addressing schemes. A common feature involves the application of a voltage, called a strobe voltage to each row or line in sequence. Coincidentally with the strobe applied at each row, appropriate voltages, called data voltages, are applied to all column electrodes. The differences between the different schemes lies in the shape of the strobe and data voltage waveforms.

Other addressing schemes are described in GB-2,146,473-A; GB-2,173,336-A; GB-2,173,337-A; GB-2,173,629-A; WO 89/05025; Harada et al 1985 S.I.D. Paper 8.4 pp 131–134; Lagerwall et al 1985 I.D.R.C pp 213–221 and P Maltese et al in Proc 1988 IDRC p 90–101 Fast Addressing for Ferro Electric LC Display Panels.

The material may be switched between its two states by two strobe pulses of opposite sign, in conjunction with a data waveform. Alternatively, a blanking pulse may be used to switch the material into one of its states. Periodically the sign of the blanking and the strobe pulses may be alternated to maintain a net d.c. value.

These blanking pulses are normally greater in amplitude and length of application than the strobe pulses so that the material switches irrespective of which of the two data waveforms is applied to any one intersection. Blanking pulses may be applied on a line by line basis ahead of the strobe, or the whole display may be blanked at one time, or a group of lines may be simultaneously blanked.

It is well known in the field of ferroelectric liquid crystal device technology that in order to achieve the highest performance from devices, it is important to use mixtures of compounds which give materials possessing the most suitable ferroelectric smectic characteristics for particular types of device.

Devices can be assessed for speed by consideration of the response time vs pulse voltage curve. This relationship may show a minimum in the switching time ($t_{min}$) at a particular applied voltage ($V_{min}$). At voltages higher or lower than $V_{min}$ the switching time is longer than $t_{min}$. It is well understood that devices having such a minimum in their response time vs voltage curve can be multiplex driven at high duty ratio with higher contrast than other ferroelectric liquid crystal devices. It is preferred that the said minimum in the response time vs voltage curve should occur at low applied voltage and at short pulse length respectively to allow the device to be driven using a low voltage source and fast frame address refresh rate.

Typical known materials (where materials are a mixture of compounds having suitable liquid crystal characteristics) which do not allow such a minimum when included in a ferroelectric device include the commercially available materials known as $S_{CE}13$ and ZLI-3654 (both supplied by Merck UK Ltd. Poole, Dorset). A device which does show such a minimum may be constructed according to PCT GB 88/01004 and utilising materials such as eg commercially available $S_{CE}8$ (Merck UK Ltd.). Other examples of prior art materials are exemplified by PCT/GB/86/00040, PCT/GB87/00441 and UK 2232416B.

Materials possessing a smectic A* ($S_A$*) phase may exhibit an electroclinic effect. The electroclinic effect was first described by S. Garoff and R. Meyer, Phys. Rev. Lett., 38, 848 (1977). An electroclinic device has also been described in UK patent application GB 2 244 766 A. This particular device helps to overcome the poor alignment problems of electroclinic (EC) devices using a surface alignment that gives a surface tilt within a small range of angles.

When a smectic A phase is composed of chiral molecules, it may exhibit an electroclinic effect. The origin of the electroclinic effect in a smectic A phase composed of chiral polar molecules has been described by Garoff and Meyer as follows. The application of an electric field parallel to the smectic layers of such a smectic A phase biases the free rotation of the transverse molecular dipoles and therefore produces a non-zero average of the transverse component of the molecular polarization. When such a dipole moment is present and coupled to the molecular chirality, a tilt of the long molecular axis (the director) is induced in a plane perpendicular to the dipole moment.

In thin samples for example 1–3 $\mu$m and with the smectic layers tilted or perpendicular with respect to the glass plates the electroclinic effect is detectable at low applied fields.

In an aligned smectic A sample a tilt of the director is directly related to a tilt of the optic axis. The electroclinic effect results in a linear electro-optic response. The electro-optic effect can manifest itself as a modulation of the effective birefringence of the device.

Electroclinic devices are useful, for example, in spatial light modulators having an output that varies linearly with applied voltage. A further advantage of EC devices is that they have high speed response times, much faster than twisted nematic type devices. Unlike ferroelectric devices the EC device is not bistable and has an output that varies linearly with applied voltage. The electroclinic effect is sometimes referred to as the soft-mode effect see G. Andersson et al in Appl. Phys. Lett., 51, 9, (1987).

In general terms, regarding the electroclinic effect, it is advantageous if on applying a small voltage there results a large induced tilt. An increase in induced tilt may result in an increase in contrast ratio. It is also advantageous if a large induced tilt can be obtained at as low a voltage as possible.

It is also advantageous if the relationship between molecular induced tilt and applied voltage is temperature independent. When an increase in applied voltage results in little or no change in induced tilt then the material being tested is generally referred to as exhibiting a saturation voltage effect.

By $S_A$* is meant a $S_A$ phase which contains some proportion of chiral molecules.

Cholesteric or chiral nematic liquid crystals possess a twisted helical structure which is capable of responding to a temperature change through a change in the helical pitch length. Therefore as the temperature is changed then the wavelength of the light reflected from the planar cholesteric structure will change and if the reflected light covers the visible range then distinct changes in colour occur as the temperature varies. This means that there are many possible applications including in the areas of thermography and thermooptics.

The cholesteric mesophase differs from the nematic phase in that in the cholesteric phase the director is not constant in space but undergoes a helical distortion. The pitchlength for the helix is a measure of the distance for the director to turn through 360°.

By definition, a cholesteric material is a chiral material. Cholesteric materials may also be used in electrooptical displays as dopants, for example in twisted nematic displays where they may be used to remove reverse twist defects, they may also be used in cholesteric to nematic dyed phase change displays where they may be used to enhance contrast by preventing wave-guiding.

Thermochromic applications of cholesteric liquid crystal materials usually use thin-film preparations of the cholesterogen which are then viewed against a black background. These temperature sensing devices may be placed into a number of applications involving thermometry, medical thermography, non-destructive testing, radiation sensing and for decorative purposes. Examples of these may be found in D. G. McDonnell in Thermotropic Liquid Crystals, Critical Reports on Applied Chemistry, Vol. 22, edited by G. W. Gray, 1987 pp 120–44; this reference also contains a general description of thermochromic cholesteric liquid crystals.

Generally, commercial thermochromic applications require the formulation of mixtures which possess low melting points, short pitch lengths and smectic transitions just below the required temperature-sensing region. Preferably the mixture or material should retain a low melting point and high smectic—cholesteric transition temperatures.

In general, thermochromic liquid crystal devices have a thin film of cholesterogen sandwiched between a transparent supporting substrate and a black absorbing layer. One of the fabrication methods involves producing an ink with the liquid crystal by encapsulating it in a polymer and using printing technologies to apply it to the supporting substrate. Methods of manufacturing the inks include gelatin microencapsulation, U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323.

The materials of the present invention may also be incorporated into polymer dispersed liquid crystal (PDLC) type devices such as those described in PCT/GB90/01947 and references therein. In such devices liquid crystal material is dispersed in a polymer matrix.

For a review of thermochromism in liquid crystals see J. G. Grabmaier in 'Applications of Liquid Crystals', G. Meier, E. Sackmann and J. G. Grabmaier, Springer-Verlag, Berlin and New York, 1975, pp 83–158.

For all the above applications it is not usual for a single compound to exhibit all of the properties highlighted, for example ferroelectric smectic liquid crystal materials generally consist of a mixture of compounds which when mixed together induce a chiral tilted smectic phase. Chiral dopants are added to a liquid crystalline mixture in order to induce the smectic mixture to become chiral smectic and to induce a Ps in the material, or if the material already possesses a Ps then the introduction of a chiral dopant should result in a change of value for Ps.

Compounds of formula III may be mixed with a wide range of hosts, for example smectic hosts to form a useful liquid crystal composition. Such compositions can have a range of Ps values. Compounds of formula III may be mixed with one or more of the types of hosts VIII–XIII. These different types of hosts may be mixed together to which the compound of general formula III may also be added.

Typical hosts include:

The compounds described in PCT/GB86/00040, eg of formula VIII

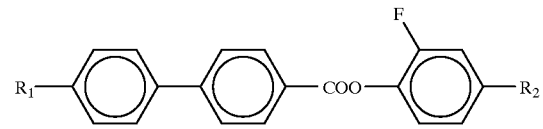

VIII where $R_1$ and $R_2$ are independently $C_3$–$C_{12}$ alkyl or alkoxy.

The fluoro-terphenyls described in EPA 84304894.3 and GBA 8725928, eg of formula IX

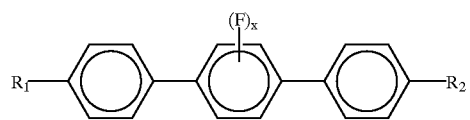

IX where $R_1$ and $R_2$ are independently $C_3$–$C_{12}$ alkyl or alkoxy, x is 1 and F may be on any of the available substitution positions on the phenyl ring specified.

The difluoro-terphenyls described in GBA 8905422.5, eg of formula X

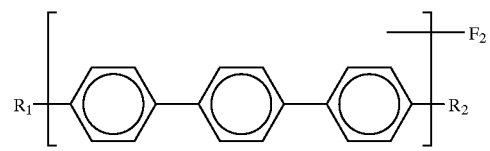

X where $R_1$ and $R_2$ are independently $C_3$–$C_{12}$ alkyl or alkoxy.

The phenyl-pyrimidines described in WO 86/00087, eg of formula XI

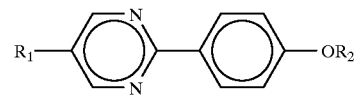

XI including those compounds where $R_1$ is $C_3$–$C_{12}$ alkyl and $R_2$ is given by the general formula $(CH_2)_n$-$CHXCH_2CH_3$, where n is 1 to 5 and X is CN or Cl.

The compounds described by R. Eidenschink et. al. in Cyclohexanederivative mit Getilteneten Smektischen Phasen at the 16$^{th}$ Freiberg Liquid Crystal Conference, Freiberg, Germany, p8. Available from E. Merck Ltd., Germany, eg of formula XII.

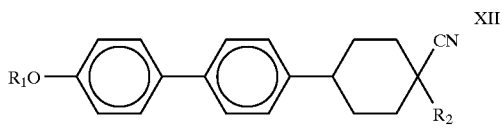

including those compounds where $R_1$ and $R_2$ are independently $C_1$–$C_{15}$ alkyl.

The difluoro-phenyl pyrimidines described in European Patent Application EP 0 332 024 A1, including the following:

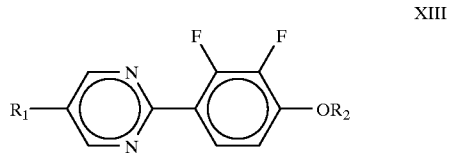

including those compounds where $R_1$ and $R_2$ are independently $C_3$–$C_9$ alkyl.

An example of the use of a compound of Formula III in a liquid crystal material and device embodying the present invention will now be described with reference to FIG. 10.

The liquid crystal device consists of two transparent plates, 1 and 2, in this case made from glass. These plates are coated on their internal face with transparent conducting electrodes 3 and 4. An alignment layer is introduced onto the internal faces of the cell so that a planar orientation of the molecules making up the liquid crystalline material will be approximately parallel to the glass plates 1 and 2. This is done by coating the glass plates 1,2 complete with conducting electrodes 3,4 with layers of film 5 and 6 of a suitable polymer, eg polyimide. The electrodes 3,4 may be formed into row and column electrodes so that the intersections between each column and row form an x, y matrix of addressable elements or pixels. Prior to the construction of the cell the films 5,6 are rubbed with a soft tissue in a given direction, the rubbing directions being arranged parallel (same or opposite direction) upon construction of the cell. A spacer 7 eg of polymethyl methacrylate separates the glass plates 1 and 2 to a suitable distance eg 2 microns. Liquid crystal material 8 is introduced between glass plates 1, 2 by filling the space in between them. The spacer 7 is sealed with an adhesive 9 in a vacuum using an existing technique. Polarisers 10, 11 may be arranged in front of and behind the cell.

The device may operate in a transmissive or reflective mode. In the former, light passing through the device, eg from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The materials of the present invention may also be useful in thermochromic devices, for example those devices described by D. G. McDonnell in Thermotropic Liquid Crystals, Critical Reports on Applied Chemistry. Vol. 22, edited by G. W. Gray, 1987 pp 120–44 and references therein.

The materials of the present invention may be mixed with nematic hosts in order to produce materials that may be used in thermochromic devices.

The compounds of Formula III may be added to host materials.

For example, H1 is a 1:1:1 mixture of the following:

$R_1=C_8H_{17}$, $R_2=C_5H_{11}$
$R_1=OC_8H_{17}$, $R_2=C_5H_{11}$
$R_1=OC_7H_{15}$, $R_2=C_7H_{15}$

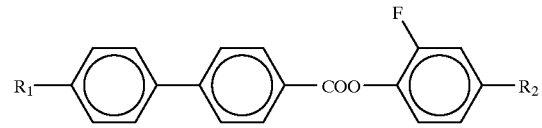

The host is a commercially available host and is widely used in ferroelectric liquid crystal mixtures.

Pyrimidine occurs in natural products. The pyrimidines cytosine, thymine and uracil are especially important because they are components of nucleic acids as are the purine derivatives adenine and guanine:

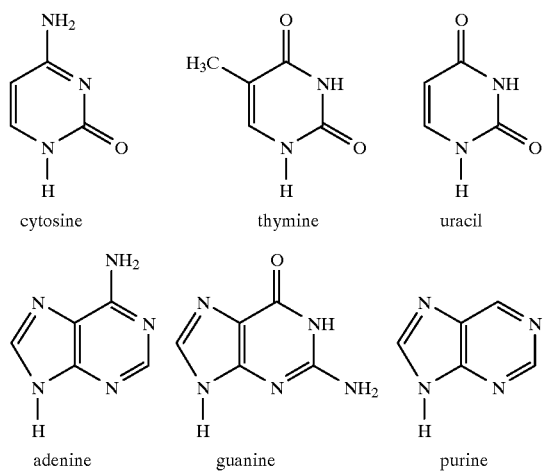

The purine nucleus also occurs in such compounds as caffeine and theobromine:

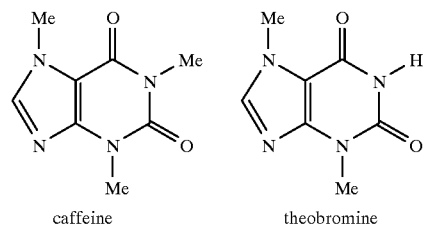

Zhang et al in J. Org. Chem. 1993, 58, 2557–2560 describe the use of pyrimidine containing compounds for the synthesis of potential human immunodeficiency virus reverse transcriptase inhibitors. Nucleosides are glycosides of heterocyclic bases, in particular of purines and pyrimidines. The nucleosides forming part of the molecule of ribose nucleic acid are the 9-β-Dribofuranoside of adenine and guanine (adenosine and guanosine) and the 3-β-D-ribofuranosides of cytosine and uracil (cytidine and uridine). In deoxynucleic acid the sugar is deoxyribose and the uracil is replaced by thymine.

In Zhang et al the following compounds (amongst others) are described:

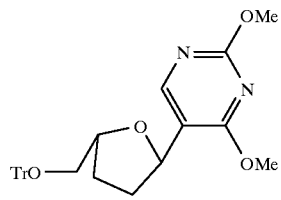

These may be described as carbon bonded nucleosides and may be important for biologically active compounds. The use of 2-iodo-5-bromopyrimidine allows for the synthesis of reversed carbon bonded nucleosides for example:

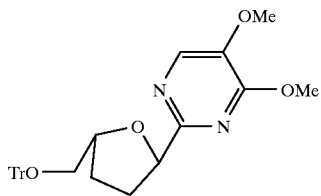

which may be of biological significance.

The above merely serve as examples for which the compound 2-iodo-5-bromopyrimidine may be used. As those skilled in the art will appreciate the uses of such a compound for the synthesis of target compounds containing one or more pyrimidine rings are very substantial.

It is also possible using 2-iodo-5-bromopyrimidine to link two or more pyrimidines together so that a molecule contains the following moiety:

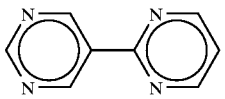

See Mikhaleva et al. Synthesis of 2,5'-substituted 2',5-bipyrimidines in Chemistry of Heterocyclic compounds, pages 671–674, 1990 Plenum Publishing Corporation.

We claim:

1. A method for the synthesis of 5-bromo-2-iodopyrimidine comprising reacting a mixture consisting essentially of a compound of formula II

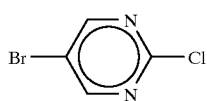

and an aqueous solution of hydrogen iodide.

2. A method according to claim 1 wherein the mixture is shaken.

3. A method according to claim 1 or 2 wherein the mixture is maintained at between −10° C. and +30° C.

4. A method according to claim 3 wherein the mixture is maintained at 0° C.

5. A method according to claim 1 wherein the mixture additionally contains a co-solvent selected from dichloromethane, chlophorm or a hydrocarbon.

6. A method of synthesizing a pyrimidine containing compound comprising reacting 5-bromo-1-iodopyrimidine with a compound comprising one of the following units

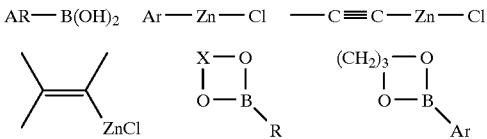

wherein Ar is an aryl group which may be substituted and X is $(CH_2)_2$ or $(CH_2)_3$.

7. A method according to claim 6 in which the pyrimidine containing compound is an optically active liquid crystal.

8. A method of synthesizing a compound of the following formula:

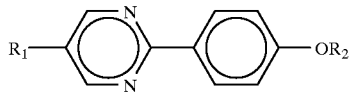

where $R_1$ is $C_3$–$C_{12}$ alkyl and $R_2$ is given by the formula $(CH_2)_n$-CHXCH$_2$CH$_3$, where n is 1 to 5 and X is CN or Cl comprising reacting 5-bromo-2-iodopyrimidine with a boronic acid.

9. A method of synthesizing a compound of the following formula:

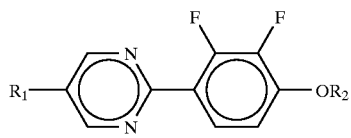

where $R_1$ and $R_2$ are independently $C_3$–$C_9$ alkyl comprising reacting 5-bromo-2-iodopyrimidine with a boronic acid.

10. A method of synthesizing a compound of the following formula:

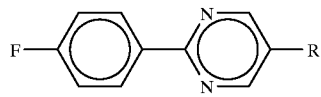

wherein R is alkyl comprising reacting 5-bromo-2-iodopyrimidine with a boronic acid.

11. A method of synthesizing a compound of the following formula:

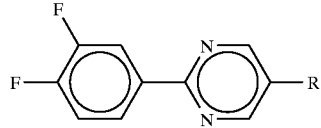

wherein R is alkyl comprising reacting 5-bromo-2-iodopyrimidine with a boronic acid.

12. A method of synthesizing a compound of the following formula:

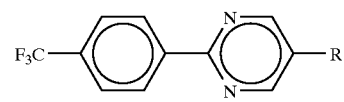

wherein R is alkyl comprising reacting 5-bromo-2-iodopyrimidine with a boronic acid.

13. A method for synthesizing a compound of the following formula:

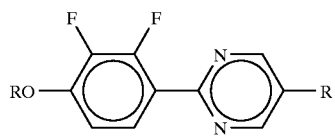

wherein both R groups are chosen from alkyl groups comprising reacting 5-bromo-2-iodopyrimidine with a boronic acid.

14. A method according to any one of claims 6 to 13 in which the reaction is conducted in the presence of a catalyst.

15. A method according to claim 14 in which the bromic acid is an arylbromic acid and the catalyst comprises palladium.

* * * * *

UNITED STATES PATENT AND TRADEMARK OFFICE

CERTIFICATE OF CORRECTION

PATENT NO.    : 5,986,096
DATED         : November 16, 1999
INVENTOR(S)   : LEWIS et al It is certified that error appears in the above-identified patent and that said letters patent is hereby corrected as shown below:

Claim 5, line 64, delete "chlorophorm" insert --chloroform--.

Claim 6, line 66, delete "-1-" insert -- -2- --.

Claim 15, line 7, delete "arylbromic" insert --arylboronic--.

Signed and Sealed this

Eighteenth Day of July, 2000

Attest:

Q. TODD DICKINSON

*Attesting Officer*    *Director of Patents and Trademarks*

UNITED STATES PATENT AND TRADEMARK OFFICE
CERTIFICATE OF CORRECTION

PATENT NO. : 5,986,096
DATED : November 16, 1999
INVENTOR(S) : Lewis et al.

It is certified that error appears in the above-identified patent and that said Letters Patent is hereby corrected as shown below:

Title page,
Item [22], should read:
-- [22] PCT Filed: Mar. 28, 1996 --.

Signed and Sealed this

Tenth Day of January, 2006

JON W. DUDAS
*Director of the United States Patent and Trademark Office*